US006566082B1

(12) United States Patent
Weinberg et al.

(10) Patent No.: US 6,566,082 B1
(45) Date of Patent: *May 20, 2003

(54) T-CELL ANTIGENS, AND THEIR USE IN DIAGNOSIS AND TREATMENT OF T-CELL MEDIATED CONDITIONS

(76) Inventors: Andrew D. Weinberg, 3266 SW. Fairmount Blvd., Portland, OR (US) 97201; Arthur A. Vandenbark, 8328 NW. Ridgetop Ct., Portland, OR (US) 97229

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/469,633

(22) Filed: Jun. 6, 1995

Related U.S. Application Data

(63) Continuation-in-part of application No. 08/192,480, filed on Feb. 4, 1994, now Pat. No. 5,759,546.

(30) Foreign Application Priority Data

Feb. 6, 1995 (WO) ............................... PCT/GB95/00237

(51) Int. Cl.[7] ...................... G01N 33/53; G01N 33/563; G01N 33/564; G01N 33/577
(52) U.S. Cl. ...................... 435/7.24; 435/7.21; 435/7.2; 435/7.1; 436/506; 436/510; 436/536; 436/811; 530/387.3; 530/387.9; 530/388.15; 530/388.22; 530/388.75; 530/389.6; 530/391.1; 530/391.3; 530/391.7; 530/866; 530/867; 530/868
(58) Field of Search ...................... 424/133.1, 135.1, 424/139.1, 142.1, 143.1, 144.1, 154.1, 173.1, 178.1, 183.1, 801, 809, 810, 1.49; 530/387.3, 387.9, 388.15, 388.22, 388.75, 389.6, 391.1, 391.3, 391.7, 866, 867, 868; 935/106, 107; 435/7, 24, 7.21, 7.1, 7.2; 436/506, 510, 536, 811

(56) References Cited

U.S. PATENT DOCUMENTS

| | | | |
|---|---|---|---|
| 4,590,071 A | 5/1986 | Scannon et al. | 424/183.1 |
| 4,664,911 A | 5/1987 | Uhr et al. | 424/182.1 |
| 4,681,760 A | 7/1987 | Fathman | 424/154.1 |
| 4,731,244 A | 3/1988 | Talle et al. | 424/154.1 |
| 4,867,973 A | 9/1989 | Goers et al. | 424/181.1 |
| 5,045,451 A | 9/1991 | Uhr et al. | 435/7.23 |
| 5,057,313 A | 10/1991 | Shih et al. | 424/1.53 |
| 5,057,598 A | 10/1991 | Pollack et al. | 424/150.1 |
| 5,091,177 A | 2/1992 | Hellström et al. | 424/1.49 |
| 5,167,956 A | 12/1992 | Neville et al. | 424/183.1 |
| 5,457,035 A | * 10/1995 | Baum et al. | 435/69.5 |
| 5,821,332 A | * 10/1998 | Godfrey et al. | 530/350 |

FOREIGN PATENT DOCUMENTS

| | | |
|---|---|---|
| WO | 8804936 | * 7/1988 |
| WO | 89/06967 | 10/1989 |
| WO | 95/12673 | 5/1995 |

OTHER PUBLICATIONS

Weinberg et al., J. Immunol., vol. 150, p. 103A, 1993.*

Schwarting et al., Section A7.1, from: "Leucocyte Typing IV White Cell Differentiation Antigens", Ed. W. Knapp et al., Oxford Univ. Press, 1992, pp. 464, 465.*

Aversa et al., Section A 8.15, from: "Leucocyte Typing IV White Cell Differentiation Antigens", Ed. W. Knapp et al., Oxford Univ. Press, 1992, pp. 498–501.*

Osband et al., Imm. Today, 11: 103–105, 1990.*

Miura et al., "Molecular Cloning and Characterization of a Novel Glycoprotein, gp34, That Is Specifically Induced by the Human T–Cell Leukemia Virus Type I Transactivator $p40^{tax}$," Mol. Cell. Biol. 11:1313–1325 (1991).

W. Godfrey et al., 'Molecular Cloning of a cDNA encoding the human homolog of the rat OX–40 antigen', p. 253, Tissue Antigens, vol. 42, No. 4, Oct. 1993, Copenhagen, Denmark.

S. Hamilton–Dutoit et al., 'An immunohistological analysis of the mAb in the activation antigen panel', p. 475–p. 476, 'Leucocyte Typing IV. White Cell Differentiation Antigens (Eds. W. Knapp et al.)' 1989, Oxford University Press, Oxford, GB.

J. Waugh et al., 'Staining of normal or rejecting kidney using the activation panel', p. 485–p. 486, 'Leucocyte Typing IV. White Cell Differentiation Antigens (Eds. W. Knapp et al.)' 1989, Oxford University Press, Oxford, GB.

N. Dunlap et al., 'Expression of activation antigens on HTLV–I and HTLV–II cell lines', p. 487–p. 488, 'Leucocyte Typing IV. White Cell Differentiation Antigens (Eds. W. Knapp et al.)' 1989, Oxford University Press, Oxford, GB.

(List continued on next page.)

Primary Examiner—Ronald B. Schwadron
(74) Attorney, Agent, or Firm—Klarquist Sparkman, LLP

(57) ABSTRACT

The OX-40 antigen is characterized and claimed together with variants and derivatives thereof. Also described are binding agents for the antigen and the use of these in diagnosis and therapy. Examples of such use include a method for the selective depletion of activated CD4[+] T-cells in vivo by using immunotoxins comprising an OX-40 antibody conjugated to a toxic molecule (such as Ricin-A chain). The administration of these specific immunotoxins is used therapeutically to deplete autoimmune reactive CD4[+] T-cells which have been implicated in diseases including Multiple Sclerosis, Rheumatoid Arthritis, Sarcoidosis, and Autoimmune Uveitis as well as inflammatory bowel disease and graft-versus-host disease. This type of therapy is also beneficial for eradicating CD4[+] T-cell lymphomas and alloreactive CD4[+] T-cells involved with a transplantation reaction. The use of the human form of the OX-40 antibody will also help in the early diagnosis of all the diseases mentioned above.

24 Claims, 9 Drawing Sheets

OTHER PUBLICATIONS

R. Vilella et al., 'Sequential appearance of the activation antigens', p. 495–p. 498, 'Leucocyte Typing IV. White Cell Differentiation Antigens (Eds. W. Knapp et al.)' 1989, Oxford University Press, Oxford, GB.

G. Aversa et al., 'Activation panel antigen expression on PBL activated by PHA or in MLR', p. 498–p. 501, 'Leucocyte Typing IV. White Cell Differentiation Antigens (Eds. W. Knapp et al.)' 1989, Oxford University Press, Oxford, GB.

P. King et al., 'Tonsillar dendritic–cell–induced T–lymphocyte proliferation: analysis of molecular mechanisms using the activation panel of mAb', p. 503–p. 505, 'Leucocyte Typing IV. White Cell Differentiation Antigens (Eds. W. Knapp et al.)' 1989, Oxford University Press, Oxford, GB.

O. Rentrop et al., 'Biochemical analysis of the workshop antibodies of the activation section', p. 473–p. 474, 'Leucocyte Typing IV. White Cell Differentiation Antigens (Eds. W. Knapp et al.)' 1989, Oxford University Press, Oxford, GB.

U. Latza et al., 'The human OX40 homolog: cDNA structure, expression and chromosomal assignment of the ACT35 antigen', pp. 677–683, European Journal of Immunology, vol. 24, No. 3, Mar. 1994, Weinheim, Germany.

W. Godfrey et al. 'Identification of a human OX–40 ligand, a a costimulator of CD4+ T cells with homology to tumor necrosis factor', pp. 757–762, The Journal of Experimental Medicine, vol. 180, No. 2, Aug. 1994, New York NY, USA.

W. Godfrey et al., 'Stan–40, a new member of the FAS–T-NFr superfamily expressed selectively on activated, human CD+ T cells', p. 355, Journal of Cellular Biochemistry, Supplement, vol. 0, No. 18D, 1994, New York NY, USA.

Calderhead et al., "Cloning of Mouse OX40: A T Cell Activation Marker That May Mediate T–B Cell Interactions," *J. Immun.* 151:5261–5271 (1993).

Holoshitz et al., "Arthritis Induced in Rats by Cloned T Lymphocytes Responsive to Mycobacteria but Not To Collagen Type II," *J. Clin. Invest.* 73:211–215 (1984).

Kennedy et al., "Analysis of Cytokine mRNA Expression in the Central Nervous System of Mice with Experimental Autoimmune Encephalomyelitis Reveals that IL–10 mRNA Expression Correlates with Recovery," *J. Immun.* 149:2496–2505 (1992).

Khoury et al., "Oral Tolerance to Myelin Basic Protein and Natural Recovery from Experimental Autoimmune Encephalomyelitis Are Associated with Downregulation of Inflammatory Cytokines and Differential Upregulation of Transforming Growth Factor β, Interleukin 4, and Prostaglandin E. Expression in the Brain," *J. Exp. Med.* 176:1355–1364 (1992).

Mallett et al., "Characterization of the MRC OX40 Antigen of Activated CD4 Positive T Lymphocytes—a Molecule Related to Nerve Growth Factor Receptor," *EMBO J.* 9:1062–1068 (1990).

Paterson et al., "Antigens of Activated Rat T Lymphocytes Including a Molecule of 50,000$M_r$ Detected Only on CD4 Positive T Blasts," *Mol. Immun.* 24:1281–1290 (1987).

Steinman Lawrence, "Autoimmune Disease," *Sci. Amer.* 9:107–114 (1993).

Vitetta et al., "Phase I Immunotoxin Trial in Patients with B–Cell Lymphoma," *Cancer Res.* 51:4052–4058 (1991).

Weinberg et al., "Transforming Growth Factor–β Enhances the in Vivo Effector Function and Memory Phenotype of Antigen–Specific T Helper Cells in Experimental Autoimmune Encephalomyelitis," *J. Immun.* 148:2109–2117 (1992).

Queen et al., "A Humanized Antibody that Binds to the Interleukin 2 Receptor," *Proc. Natl. Acad. Sci.* 86:10029–10033 (1989).

Lohse and Cohen, "Immunoregulation: Studies of Physiological and Therapeutic Autoreactivity by T Cell Vaccination," *Springer Semin. Immunopathol.* 14:179–186 (1992).

Chatterjee et al., "Idiotypic Antibody Immunotherapy of Cancer," *Cancer Immunol. Immunother.* 38:75–82 (1994).

Harris et al., "Therapeutic Antibodies—The Coming of Age," *TibTech* 11:42–44 (1993).

Emery and Adair, "Humanized Monoclonal Antibodies for Therapeutic Applications," *Exp. Opin. Invest. Drugs* 3:241–251 (1994).

Winter and Harris, "Antibody–Based Therapy, Humanized Antibodies," *TIPS* 14:139–143 (1993).

Kahan, "Immunosuppressive Therapy," *Cur. Opin. Immunol.* 4:553–560 (1992).

Borrebaeck et al., "Does Endogenous Glycosylation Prevent the Use of Mouse Monoclonal Antibodies as Cancer Therapeutics?," *Immunol. Today* 14:477–482 (1993).

Waldmann, "Monoclonal Antibodies in Diagnosis and Therapy," *Science* 252:1657–1662 (1991).

Parker et al., "Fusion Proteins in Immunotherapy," *Trans. Proc.* 24:2362–2365 (1992).

Baum et al., Molecular characterization of murine and human OX40/OX40 ligand systems: identification of a human OX40 ligand as the HTLV–1–regulated protein gp34, The EMBO Journal, 13(17):3992–4001 (1994).

Mallett et al., A new superfamily of cell surface proteins related to the nerve growth factor receptor, Immunology Today 12(7):220–223 (1991).

Weinberg et al., Target organ–specific up–regulation of the MRC OX–40 marker and selective production of Th1 lymphokine mRNA by encepahalitogenic T helper cells isolated from the spinal cord of rats with experimental autoimmune encephalomyelitis, J. Immunol., 152(9):4712–21 (1994).

* cited by examiner

FIG. 3 Vβ Profile of OX-40 Presorted. Negative and Positive at Onset of EAE

FIG. 6A Exotoxin-OX-40 F1

FIG. 6B Exotoxin OX-40 Lewis

Ox-40 Immunotoxin Treatment
Effect on Donor +T-cell Isolated From the Spinal Cord

```
ATG TGC GGG GTG TGC GCT GGG CGG CTG GGC CGC GGG CCG TGT GCG GCT CTG CTC CTG GGC
met cys gly val cys ala gly arg leu gly arg gly pro cys ala ala leu leu leu gly CTG GGG TGC CTG ACC GTG ACG GGG CTC CAC TGT GTC GAC ACC TAC CCC AGC CTC AAC GAC
leu gly cys leu thr val thr gly leu his cys val asp thr tyr pro ser leu asn asp CGG TGC TGC CAC GAG TGC AGG CCG AAC GGC TGT ATG GGG AGC AGC CCC AGC AGC CCC CAG
arg cys cys his glu cys arg pro asn gly cys met gly ser ser pro ser ser pro gln AAC ACG CGT CGT ACG AGG GGG CCG GTG TTC ATG TAC GGG AGC CAG AGC TCC CGG CCG
asn thr arg arg thr arg gly pro val phe met tyr gly ser gln ser ser arg pro TGC GCC GAC CAG GTT GCC ACA GTC GGG GCG GCC TGG TGG GCT CCA CTA CGA GCC GGT
cys ala asp gln val ala thr val gly ala ala trp trp ala pro leu arg ala gly GCC GGA GAT GAC TGG GCA ACC ATC GTG CTG CCC GAC CCG CAG CCC CAG AGA GCC GGA TTC
ala gly asp asp trp ala thr ile val leu pro asp pro gln pro gln arg ala gly phe ACC CGG AGG GAG GAT GAC
thr arg arg glu asp asp

TGA
OPA
```

FIG. 11

T-CELL ANTIGENS, AND THEIR USE IN DIAGNOSIS AND TREATMENT OF T-CELL MEDIATED CONDITIONS

CROSS REFERENCE TO RELATED APPLICATION

This application is a continuation-in-part of U.S. patent application Ser. No. 08/192,480, filed on Feb. 4, 1994, now U.S. Pat. No. 5,759,546 which is herein incorporated by reference.

TECHNICAL FIELD

This invention relates to methods for the specific depletion of activated T-lymphocytes particularly those belonging to the $CD4^+$ subclass. Such activated T-lymphocytes e.g. $CD4^+$ T-lymphocytes, are implicated in a number of conditions in humans including multiple sclerosis and transplant rejection. In particular, this invention provides a treatment in which activated T-lymphocytes e.g. $CD4^+$ T-cells involved in a particular disease or condition are depleted while the non-activated T-lymphocyte e.g. $CD4^+$ T-cells repertoire is unaffected.

BACKGROUND OF INVENTION

The $CD4^+$ T-lymphocyte (herein referred to as the $CD4^+$ T-cell) is the central player in the immune system because of the "help" it provides to other leukocytes in fighting off infection and potential cancerous cells. $CD4^+$ T-cells play essential roles in both humeral and cell-mediated immunity and additionally they act during parasite infection to promote the differentiation of eosinophils and mast cells. If the $CD4^+$ T-cell population is depleted (as is the case in AIDS patients) the host is rendered susceptible to a number of pathogens and tumours that do not ordinarily pose a threat to the host.

While $CD4^+$ T-cells thus play an important beneficial role in disease prevention, the aberrant function of these cells can produce serious problems. In some individuals, the aberrant function of $CD4^+$ T-cells leads to autoimmunity and other disease states (Swanborg, R. H., 1984; Cush, J. J., and Lipsky, P. E., 1988; Caspi et al., 1988). Autoimmune diseases in which $CD4^+$ T-cells have been implicated include multiple sclerosis, rheumatoid arthritis and autoimmune uveitis (see generally, Steinman, L., 1993). In essence these diseases involve an aberrant immune response in which the immune system is subverted from its normal role of attacking invading pathogens and instead attacks the host body tissues, leading to illness and even death. The targeted host tissues vary between autoimmune diseases, for example, in multiple sclerosis the immune system attacks the white matter of the brain and spinal cord, in rheumatoid arthritis the immune system attacks the synovial lining of the joints. Activated $CD4^+$ T-cells have also been implicated in other illnesses, including rejection of transplant tissues and organs and in the development of $CD4^+$ T-cell lymphomas.

Investigations into conditions caused by aberrant $CD4^+$ T-cell activity are focused on several animal models, and in particular on a number of experimentally induced autoimmune diseases. Research on these experimentally induced diseases in animals is premised on the idea that they will provide information useful in the treatment of the corresponding human diseases. In pursuit of this goal, it has been shown that $CD4^+$ T-cells are responsible for several experimentally induced autoimmune diseases in animals, including experimental autoimmune endephalomyelitis (EAE), collagen induced arthritis (CIA), and experimental autoimmune uveitis (EAU).

EAE is induced by autoimmunizing animals against myelin basic protein (MBP, a component of the white matter of the brain and the spinal cord) and produces the same clinical symptoms observed in multiple sclerosis: demyelination and paralysis. Proof of the value of the EAE model as a comparative model for multiple sclerosis has been provided by evidence showing that these conditions share a causative nexus: Steinman and co-workers showed that the predominant cell type found in the brain lesions of multiple sclerosis patients is $CD4^+$ T-cells (Oksenberg, J. R., et al., 1990) and that the T-cell receptor (the molecule responsible for antigen recognition) associated with the cells in these brain lesions had the same 3 amino acid binding motif for antigen recognition as on the $CD4^+$ T-cells responsible for causing experimental autoimmune. encephalomyelitis (EAE) (Oksenberg, J. R., et al., 1993). All the evidence thus suggests that the EAE model will be useful in testing therapies for multiple sclerosis.

Research on a number of the experimentally induced autoimmune diseases, including EAE, CIA and EAU, has shown that antibodies that bind $CD4^+$ T-cells when injected in vivo can inhibit the development of these diseases as well as inhibit transplantation rejection (Swanborg, R. H. 1983; Cobbold, S. P. et al., 1984; Steinman, L, 1993). This antibody-mediated effect depletes or inactivates all $CD4^+$ cells in the body (the antibodies that bind to the $CD4^+$ cells presumably block the activity of the cells and also target the $CD4^+$ cells for destruction by the immune system.) This strategy has shown some success with rheumatoid arthritis and is now being tested for multiple sclerosis (see generally, Steinman, L., 1993).

While it appears that therapeutic approaches that destroy the $CD4^+$ T-lymphocyte population might be effective in ameliorating these autoimmune diseases, this approach has one very major drawback. The treatment not only inhibits the function of those $CD4^+$ T-cells that are antigen reactive and thus involved in the autoimmune disease process, but also the $CD4^+$ T-cells that are quiescent and not involved in the disease. Since $CD4^+$ T-cells are important in the general immune response (protecting the body against infectious agents), destruction of the entire $CD4^+$ T-cell population leaves the patient severely immunocompromised and hence highly susceptible to infection. A preferable approach would be to remove only those $CD4^+$ T-cells that are actively involved in the auto-immune response, leaving the remaining $CD4^+$ T-cell population available for their normal role in the immune system.

This method of treatment has not yet been achieved. It is therefore an object of the present invention to provide a method of specifically depleting the population of activated $CD4^+$ T-cells in a patient without affecting the quiescent $CD4^+$ T-cell population.

SUMMARY OF THE INVENTION

In one aspect the present invention provides a method by which autoantigen specific T-cells, especially for example activated $CD4^+$ T-cells, can be specifically eliminated in vivo, while leaving the quiescent population of T-cells especially for example unactivated $CD4^+$ T-cells intact. This invention therefore provides a treatment useful for T-cell mediated especially for example activated $CD4^+$ T-cell mediated autoimmune diseases such as multiple sclerosis, rheumatoid arthritis, sarcoidosis and autoimmune uveitis, graft versus host disease (GVHD) and/or inflammatory bowel disease. This invention also provides a method for eliminating other undesired immune responses caused by activated T-cells especially for example activated CD4+ T-cells such as rejection of transplanted tissue and organs in transplant recipients. Furthermore, the present invention provides a method of specifically eliminating activated CD4+ T-cell lymphomas from the body. The present invention also provides a method for early diagnosis of conditions mediated by activated T-cells especially for example activated CD4+ T-cells by detecting the presence of autoreactive T-cells at the site of autoimmune lesions and potentially harmful T-cell lymphomas. This early diagnosis provides an indication that the methods of treatment provided by the present invention may be effective and can facilitate earlier treatment of the condition than might otherwise be possible.

The present invention is also based on the discovery that a particular protein antigen, termed OX-40 (herein referred to as the OX-40 antigen), is specifically expressed on the cell surface of antigen activated T-cells especially for example activated CD4+ T-cells. In particular, using the EAE disease model in rats, this antigen was shown to be expressed on the surface of activated autoantigen-specific CD4+ T-cells present at the site of inflammation (the spinal cord in this disease model) but absent on CD4+ T-cells at non-inflammatory sites. Furthermore, the highest expression of this antigen on these CD4+ T-cells was found to occur on the day prior to initiation of clinical signs of autoimmunity; the expression of this antigen decreased as the disease progressed. The specificity of expression of the OX-40 antigen and the transient nature of this expression, shown for the first time in the present invention, motivated the testing of this antigen as a possible target for antibody mediated depletion of activated T-cells in animals such as humans with T-cell mediated conditions.

The applicants have cloned and sequenced the cDNA encoding the OX-40 antigen. Thus the invention provides a nucleic acid having the sequence shown in Seq ID No 1 or a sub-sequence of SEQ ID No 1 which encodes an antigenic polypeptide; or a variant or allele thereof; or a complementary strand to any of these. A particular sub-sequence of SEQ ID No 1 comprises nucleotide bases 15 to 848 shown in Seq ID No 1 or its complementary strand.

Further according to the invention there is provided a polypeptide comprising an amino acid sequence encoded by a nucleic acid as described above or a derivative thereof. Suitably the polypeptide comprises an amino acid sequence encoded by a sub-sequence of the sequence shown in SEQ ID No 1 and which includes an antigenic determinant.

Among the variants of nucleic acid sequences and polypeptides contemplated by the invention are (for example) DNA sequence variants importing no change in encoded amino acid sequence. Then there are (for further example) sequence variants importing "conservative" amino acid changes eg changes from one acidic amino acid to another, one aromatic amino acid to another, one basic amino acid to another, one aliphatic hydrophobic sidechain to another, as is well known in the art. Then there are for example variants corresponding to allelic variants in the encoded polypeptide, and other variants that result in polypeptides of antigenic cross-reactivity and/or similar binding specificity.

The antigenicity of the polypeptides and variants mentioned in the specification includes for example antigenic determinants shared or cross-reactive with the OX-40 antigen as encoded by Seq ID No. 1, eg antigenic polypeptides with determinants that are shared with determinants of OX-40 that are accessible to specific binding agents when the OX-40 is present on a cell surface.

Simply finding a target antigen on a particular cell type does not provide a basis for a therapeutic approach which requires depleting the particular cell type. Thus, many antigens are shed from the cell surface and are not suitable as targets for therapy. A further aspect of this invention is the discovery that a specific binding agent such as an antibody raised against the OX-40 protein and conjugated to a cytotoxin can inhibit the in vitro proliferation of antigen activated CD4+ T-cells. This discovery implies that the OX-40 antigen is rapidly internalized by CD4+ T-cells. Additional research based on this discovery led to an important focus of the present invention; a demonstration that a population of antigen activated CD4+ T-cells can be depleted in vivo by conjugating a specific binding agent such as an antibody raised against the OX-40 antigen with a cytotoxin to produce an immunotoxin, and administering this immunotoxin to a host. In this manner, the antibody binds to the OX-40 antigen on the surface of the activated CD4+ T-cell. Internalization of the immunotoxin results in the cytotoxin being taken into the cell, which produces cell death. Hence, administration of this immunotoxin to a host suffering from activated T-cell (eg CD4+ T-cell) mediated inflammation depletes (or otherwise inactivates) the activated T-cells especially for example activated CD4+ T-cells at the site of inflammation or other sites, leading to amelioration of subsequent inflammation and/or other clinical signs of disease.

A further aspect of the present invention is therefore a method of treating a patient suffering from a condition mediated by activated T-cells e.g. CD4+ T-cells, which comprises administering to the patient an effective amount of a specific binding agent which can specifically bind to a polypeptide as described above, eg an antibody, conjugated with a cytotoxic agent or a radionuclide, and wherein the antibody recognises and binds to the OX-40 antigen present on the surface of the T-cells, especially for example activated CD4+ T-cells.

Particular methods of the invention include a method for reducing a population of T-cells, e.g. CD4+ T-cells that express an OX-40 antigen in a human host and a method of inhibiting relapsing autoimmune inflammation in a patient suffering from multiple sclerosis, which methods comprise administering an effective amount of a specific binding agent of the invention.

In particular the specific binding agent used in these methods is an antibody conjugated with a cytotoxic agent or a radionuclide wherein the antibody recognizes and binds to the OX-40 antigen present on the surface of the T-cells especially for example activated CD4+ T-cells. Alternatively the method may employ a specific binding agent which comprises a Fab, F(ab')2, or Fv fragment of a monoclonal antibody capable of recognising Ox-40 antigen when expressed on the surface of T-cells. Other specific binding agents useful in this method are immunoglobulins capable of cytotoxic effect on cells bearing Ox-40 on their surface or any specific binding agents which can fix, complement or mediate antibody-dependant cellular cytotoxicity such as a specific binding agent which has or is linked to structure characteristic of the Fc region of an immunoglobulin of murine type IgG2a or human type IgG1 or IgG3.

The methods of the invention are applicable to any condition mediated by activated T-cells especially for example activated CD4+ T-cells, including, multiple sclerosis, sarcoidosis, rheumatoid arthritis, autoimmune uveitis, T-cell lymphomas and rejection of a transplanted organ or tissue. Additional conditions to which this method is applicable include graft-versus-host disease or reaction and inflammatory bowel disease.

T-cells can be activated by for example antigens, superantigens, mitogens, or monoclonal antibodies.

The methods of treatment set forth in the preceding paragraph will preferably be performed using specific binding agents such as monoclonal antibodies, or fragments thereof, which can be raised using the polypeptides of the invention. In a more preferred embodiment, the monoclonal antibody will be a humanized monoclonal antibody. In alternative embodiments, the method will utilize a cytotoxic conjugate, eg comprising a fragment such as a Fab, F(ab')$_2$ or Fv fragment of a monoclonal antibody conjugated with a cytotoxic agent wherein the fragment of the monoclonal antibody recognizes the OX-40 antigen.

This invention also encompasses specific binding agents such as monoclonal antibodies having a specificity of binding in cells to substantially only antigen activated T-cells especially for example activated CD4$^+$ T-cells. In a preferred embodiment, the specific binding agents can specifically bind to a polypeptide of the invention. Particular specific binding agents specifically bind to human Ox-40 of amino acid sequence encoded by the coding region of nucleic acid sequence Seq ID No 1, when said Ox-40 is present on the surface of activated cells.

These specific binding agents suitably comprise an antibody binding domain and are preferably monoclonal antibodies or binding fragments thereof. As mentioned above, the antibodies will preferably be at least partially humanised, and so most preferably comprise a humanised monoclonal antibody.

"Specific binding" refers for example to specific non-covalent molecular binding such as that between an antibody and a corresponding antigen or hapten (its "binding partner") and also between other specialised binding molecules and their binding partners.

"At least partly humanised", relating to antibodies and their binding domains, means that for example embodiments are contemplated in which only the constant region (CH and CL) may correspond to human polypeptide: alternatively, both the constant and variable regions may be "humanised".

Another aspect of this invention provides a specific binding agent such as a monoclonal antibody as described above which further comprises a molecularly linked, eg covalently conjugated, cytotoxin. Antibody-cytotoxin conjugates (also known as immunotoxins) are suitable for use in the methods of treatment described above. Examples of such specific binding agents include Fab, F(ab')$_2$ or Fv fragments of a monoclonal antibody conjugated with a cytotoxic agent.

For therapeutic use, the specific binding agents of the invention are suitably administered in the form of a pharmaceutical composition which include a pharmaceutically acceptable carrier. The carrier may be solid or preferably liquid carriers such as water or saline, which are conventional in the art.

A further aspect of the invention comprises a method of detecting a condition mediated by activated T-cells, e.g CD4$^+$ T-cells, in a patient comprising contacting a specific binding agent as described above with said T-cells and quantifying the level of activated T-cells. Suitably the method is carried out on a biopsy sample from the patient, such as a skin or intestinal biopsy sample or a blood sample from a patient suspected of having a graft-versus-host disease, or an intestinal biopsy sample from a patient suspected of having an inflammatory bowel disorder, or a sample of cerebrospinal fluid.

A further aspect of the present invention is a method of detecting an inflammatory condition mediated by activated T-cells especially for example activated CD4$^+$ T-cells in a patient by obtaining a suitable biopsy sample from the patient and then quantifying the percentage of activated T-cells especially for example activated CD4$^+$ T-cells in the biopsy sample using a specific binding agent such as an antibody that specifically binds to the OX-40 antigen. Other aspects of the present invention include test kits for detecting conditions mediated by activated T-cells especially for example activated CD4$^+$ T-cells, and treatment kits comprising antibody in pharmaceutically administrable forms and amounts with suitable excipients and containers.

In particular the invention provides a kit for detecting a condition mediated by activated T-cells e.g. CD4$^+$ T-cells in a patient comprising a specific binding agent as described above which is labelled. Preferably the invention provides a kit for carrying out a specific binding assay for detection or quantitation of an analyte that comprises a polypeptide or a specific binding agent as described above, wherein said kit comprises a first reagent comprising a specific binding agent that can recognise the analyte, a second reagent comprising a substance that can bind specifically either to the analyte or to the first reagent, and a label for the second reagent.

In such a kit the first reagent can comprise an antibody specific for the analyte, and the second reagent comprises a labelled antiglobulin specific for the first reagent.

Alternatively the first reagent can comprise an immobilised specific binding reagent for the analyte, then the second reagent is a specific binding agent that can bind to the analyte when the analyte is also bound to the first reagent.

In a further embodiment wherein the second reagent comprises a substance able to compete with analyte for binding to the first reagent.

For use in this method, the specific binding agent may further comprises a label such as a radioactive label or a fluorescent label and these specific binding agents form a further aspect of the invention.

The specific binding agents of the invention may be cloned and sequenced in the usual way. Thus the invention further provides a nucleic acid sequence encoding the amino acid sequence of a specific binding agent as described above.

Recombinant technology may be used to prepare both the polypeptides and the specific binding agents of the invention. Thus appropriate expression vectors, transformed host organisms and methods of preparation which include culturing a host organism form further aspects of the invention.

The OX40 binding agent, for instance an anti-OX40 monoclonal antibody, can be administered to those patients suffering from a disease mediated by activated T cells e.g. graft-versus-host disease. The amount administered will depend on the amount required to produce an improvement, either partial or total, in the patient's symptoms. This will depend not only on the severity of the condition and route of administration but also on the administration of other therapeutic agents (eg glucocorticoids, cyclosporine A, prednisolone). The OX40 binding agent may be injected either systemically (eg intravenous) or locally (eg intramuscular). As discussed elsewhere the OX40 binding agent may be coupled to a toxic substance for maximum therapeutic effect.

OX-40 and Graft Versus Host Disease (GVHD)

In the case of GVHD, immunocompetent T cells derived from the donor tissue or cells attack recipient tissue including skin, gut and liver, which are severely compromised in their ability to carry out their normal function. Such attacks, if not controlled, can lead to death of the patient. The therapeutic agents of the present invention could be used to block the activation of or to eliminate the donor T cells thereby preventing or halting the disease process.

OX-40 and GvHD: Diagnostics

The present invention can be used in diagnostic tests and procedures in vitro. For instance the OX40 binding agent can be used to determine the presence of OX40+ T cells in a biopsy sample from a patient. The biopsy sample may be a tissue sample or a sample of blood. Mononuclear cells are isolated from the blood or tissue according to standard techniques (see Practical Immunology. L. Hudson and F. C. Hay, eds. Blackwell Scientific Publications, Oxford) and stained with an anti-OX40 antibody or OX40 binding agent fusion protein. The presence of the OX40 binding agent is then detected with an anti-globulin reagent coupled with a fluorochrome such as fluoroscein isothiocyanate or phycoerythrin and the number of positive cells analysed on a flow cytometer or by fluorescence microscopy (see eg Practical Flow Cytometry. Shapiro, H. M., ed. Alan R Liss, New York; Practical Immunology. L. Hudson and F. C. Hay, eds. Blackwell Scientific Publications, Oxford). Alternatively the tissue sample is processed for immunohistochemical staining by standard techniques (see eg Immunocytochemistry: Practical Applications in Pathology and Biology. J. Polak and S. van Noorden, eds. John Wright and Sons, Bristol). The OX40+ population of cells could be further characterised by two- or three-colour flow cytometry or immunohistochemistry (see eg Practical Flow Cytometry. Shapiro, H. M., ed. Alan R. Liss, New York; Immunocytochemistry: Practical Applications in Pathology and Biology. J. Polak and S. van Noorden, eds. John Wright and Sons, Bristol). Detection of OX40+ cells can aid in the diagnosis and management of diseases caused by activated T cells e.g. inflammatory bowel disease and GvHD and may be used to follow the course of the disease: an increase in the proportion of OX40+ cells would suggest a worsening of the disease and may indicate the need to increase the dose of therapeutic agent being administered, while a decrease in the proportion of OX40+ cells would suggest an improvement and thus indicate a diminution in the amount of therapeutic agent being administered.

Determination of the levels of OX40+ cells in the blood of patients at risk of GvHD (eg following allogenic bone-marrow transplantation) may allow one to predict the imminent onset of GvHD. Early administration of immunosuppressive agents to control GvHD will improve the likelihood of successful treatment.

The present invention can be used in diagnostic tests and procedures in vivo. For instance, the administration of an OX40 binding agent coupled to a radioisotope can be used for the purposes of immunoscintigraphy.

These and other aspects of the present invention will become more readily apparent from the following figures and description of the invention.

DESCRIPTION OF THE DRAWINGS

FIG. 6A and FIG. 6B are two graphs showing dose dependent inhibition of antigen specific $CD4^+$ T-cell proliferation by the OX-40-exotoxin conjugate. Varying concentrations of the OX-40-exotoxin was added to a constant amount of F1 T-cells (FIG. 4A) or Lewis T-cells (FIG. 4B), APC, and MBP. The open bars (to the right of the graphs) show the proliferation (represented by [$^3$H]-thymidine incorporation) of these T-cells with and without antigen (Pos and Neg respectively). The assay was carried out in a 200 µl volume.

FIG. 11 shows the nucleotide sequence of the coding region of the human OX-40 cDNA and the theoretical amino acid sequence of the human OX-40 antigen. These sequences are encompassed within SEQ I.D. No. 1 set forth in the accompanying sequence listing.

DETAILED DESCRIPTION OF THE INVENTION

Figure 1:
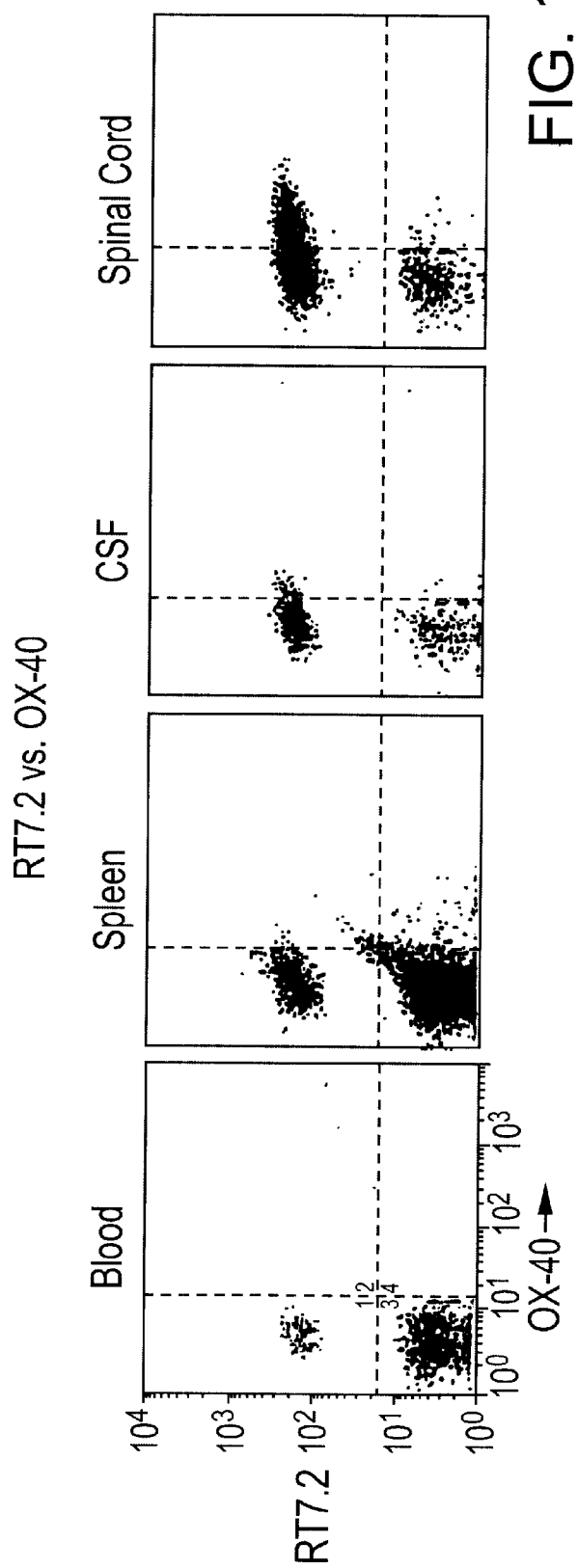
FIG. 1 shows dot plots from a fluorescence activated cell sorting (FACS) apparatus showing tissue specific dual expression of RT7.2 and the MRC OX-40 antigen. Lymphocytes were isolated from the various tissue compartments designated in the figures during the onset of EAE. The cells were stained with the OX-40 antibody conjugated to fluorescein isothiocyanate (FITC) displayed on the x-axis and counterstained with a R-phycoerythrin (PE) conjugated to the RT7.2 antibody displayed on the y-axis. An isotype matched control antibody was used to draw the quadrants for both the FITC and PE conjugated Abs. The OX-40 antibody was 50% positive on the donor T-cells isolated from the spinal cord, and 8, 2, and 1.8% positive for the donor cells isolated from the CSF, spleen, and blood respectively.

The present invention provides, for the first time, a method of eliminating undesired immune responses caused by antigen activated T-cells especially for example activated CD4$^+$ T-cells. Without wishing to be bound by theory, the inventors made the invention after making findings suggestive that a cell surface antigen, herein termed the Ox-40 antigen, is upregulated solely or preferentially on activated T-cells, especially for example activated CD4$^+$ T-cells found at the site of inflammation, and that this cell surface antigen appears to be internalized rapidly. Based on this discovery, a therapeutic method has been developed which utilizes antibodies which bind to the OX-40 protein (herein termed OX-40 antibodies) linked to cytotoxins, to destroy cells expressing the OX-40 antigen. This type of therapy will be extremely useful because it is targeted only to activated T-cells especially for example activated CD4$^+$ T-cells and leaves the rest of the T-cell repertoire intact.

Activated T-cells especially for example activated CD4$^+$ T-cells have been implicated in a number of antigen activated autoimmune diseases, including multiple sclerosis, sarcoidosis, rheumatoid arthritis and autoimmune uveitis, as well as in transplantation rejections. (Swanborg, R. H., 1984; Cush, J. J., and Lipsky, P. E., 1988; Caspi et al, 1988; Cobbold, S. P. et al., 1984.) CD4$^+$ T-cell lymphomas have also been shown to have an activated phenotype (Gootenberg, J. E. et al., 1981). The present invention provides both methods of diagnosis and methods of treatment for these and other conditions mediated by activated T-cells especially for example activated CD4$^+$ T-cells. More particularly, and following the description of relevant materials and methods used in this invention, experimental data obtained during the development of the present invention is presented. These data demonstrate that the OX-40 protein is exclusively expressed at the site of autoimmune inflammation in rats with EAE on the surface of myelin basic protein (MBP) activated CD4$^+$ T-cells. It is further shown that the proliferation of MBP activated CD4$^+$ T-cells can be inhibited in vitro using an OX-40 antibody conjugated with a Ricin dgA cytotoxin. This inhibitory activity is shown not to be limited to MBP activated cells, but also to be effective in inhibiting the proliferation of CD4$^+$ T-cells activated by other antigens, including an antigen derived from *Mycobacterium tuberculosis*. The OX-40 antibody-cytotoxin conjugate is shown to be effective in vivo; use of the conjugate is shown to inhibit the clinical development of EAE. Following this, the cloning of the human OX-40 homolog is presented along with the production of monoclonal antibodies to the human OX-40 protein.

Various examples are presented showing the application of the present invention. Specifically, Example 1 describes preferred methods of producing the human OX-40 cDNA enabled by the present invention. Example 2 describes methods of producing purified human OX-40 protein, and Example 3 describes the production of monoclonal and polyclonal antibodies that recognize the human protein. Example 4 describes the production of immunotoxins, based on these monoclonal antibodies, that are suitable for therapeutic use in humans, and other antibody conjugates suitable for diagnostic use. Example 5 describes the use of human OX-40 monoclonal antibodies in diagnosing activated CD4$^+$ T-cell mediated conditions and Example 6 describes the use of the immunotoxins in therapeutic applications. Example 7 describes kits for the diagnosis and treatment of activated CD4+ T-cell mediated conditions.

Materials and Methods

Animals

Lewis and Buffalo rats were obtained from Harlan Sprague-Dawley, Inc., Indianapolis, Ind. Twelve week old Lewis females were bred with 12 week old Buffalo male rats to generate the F1 Lewis×Buffalo hybrid animals. These F1 progeny were used at 8 to 12 weeks of age for MBP immunization. The rats were housed under germ-free conditions at the VA Medical Center Animal Care Facility, Portland, Oreg. according to institutional guidelines.

Selection of MBP Specific F1 and Lewis CD4+ Lymphocyte Lines

T lymphocyte lines were selected on day 12 after immunization with myelin basic protein (MBP). Details of this procedure were described earlier (Vandenbark, A. A., et al., 1985). Briefly, a lymph node cell suspension was incubated with MBP (30 μg/ml) in RPMI 1640 with 1% autologous rat serum. After 3 days at 37° C. in a 7% $CO_2$ atmosphere the cells were cultured in RPMI with 10% horse serum and IL-2. The T-cell lines were maintained in this medium until the rate of division slowed. At this point (7–14 days after MBP stimulation) the cells were restimulated with 10 μg/ml of MBP presented by irradiated Lewis thymocytes, and subsequently expanded further in IL-2 containing medium.

Adoptive Transfer of EAE

Activation of the F1 or Lewis T-cell lines for passive transfer of EAE was carried out in 10 $cm^2$ culture dishes using $5 \times 10^6$ T-cells, $100 \times 10^6$ irradiated APC, and 10 μg/ml MBP in 10 ml of medium. After three days of activation the blasts were counted and $5-10 \times 10^6$ T-cell blasts were injected with the associated APC population i.p. into irradiated (600 rads for the F1 into Lewis transfers). or non-irradiated naive Lewis rats. The naive allogeneic recipients were irradiated the day before adoptive transfer. The recipient rats were inspected daily, and the clinical signs of disease were recorded and scored as follows EAE: 0=no signs; 1=flaccid tail; 2=ataxia; 3=hindquarter paralysis; 4=quadripiegic/moribund.

Cell Collection

Cerebrospinal fluid (CSF) was collected by performing cisterna magna puncture using a 27 ga×⅜" needle with 8" tubing (Abbott Hospitals, Inc., Chicago, Ill.). The CSF was diluted in RPMI 1:4 and viable cell numbers were counted. On average, 100 μl/rat were collected. Samples were excluded if the RBC/WBC ratio exceeded 2:1. The blood was obtained by heart puncture and the lymphocytes were separated on Ficoll-Hypaque as described by Kruisbeek, A. M., 1992. The spleen cells were pushed through a wire mesh screen and the RBCs were lysed by the $NH_4Cl$ method (Kruisbeek, A. M. 1992).

Spinal Cord Lymphocyte Isolation

Spinal cord mononuclear cells were isolated following a modified version of a published protocol (Bourdette, D. N. et al., 1991). Briefly, spinal cords were isolated by insufflation, washed 3× in RPMI in order to remove any contaminating blood cells, homogenized, and then passed through a wire mesh screen. The cells were then washed and resuspended in isotonic Percoll (80%). For each individual spinal cord a 10 ml step gradient was poured into a 15 ml conical tube. Each step gradient had 100% (2 ml), 80% (4 ml), and 40% (4 ml) isotonic Percoll and the cells were layered as part of the 80% fraction. The interface between the 80/40% Percoll steps was harvested and the cells were directly spun down and washed. The lymphocytes obtained at this interface contained both the resting and blasting populations as assessed by forward scatter. A typical yield of lymphocytes obtained from the spinal cord of animals with EAE was usually $0.5-1.5 \times 10^6$ cells. Lymphocyte recovery was fairly consistent throughout the disease time course, and decreased during the last day of the recovery phase of EAE to ½ or ⅓ of the maximal cell number.

Fluorescence Activated Cell Sorting (FACS) Analysis

Figure 2:
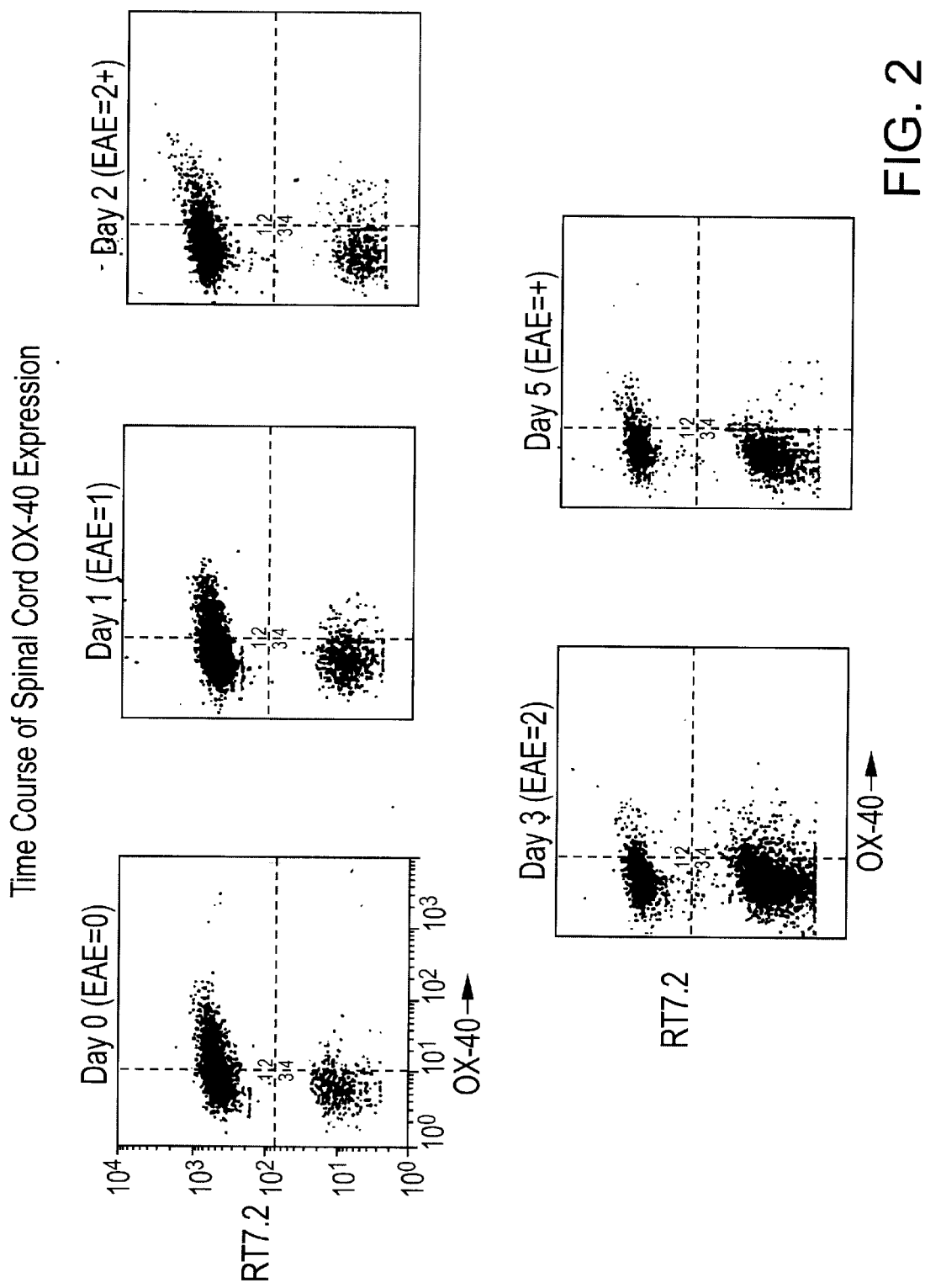
FIG. 2 shows dot plots from a FACS apparatus showing a time course of OX-40 expression on donor T-cells isolated from the spinal cords of rats with EAE. Lymphocytes were isolated from the spinal cords of rats during the time course of disease. The cells were stained with the OX-40 antibody (FITC) and counter-stained with a PE conjugated RT7.2 antibody. An isotype matched control antibody was used to draw the quadrants for both the FITC and PE conjugated Abs. The day of the EAE time course for each dot plot is indicated on the top of the graphs and the disease score (the severity of the clinical signs and disease score is provided in the methods section under "Adoptive transfer of EAE") is shown in parenthesis next to the day of disease. The percentage of $RT7.2^+$ cells were 77, 75, 81, 37, and 52% respectively for Days 0, 1, 2, 3, and 5 after disease onset. The OX-40 antibody was 54% positive for the donor T-cells on Day 0 (day before onset) and 41, 30, 18, and 12% positive on days 1, 2, 3, and 5 respectively. On Day 5 the EAE score of "+" means the animal had minimal clinical signs of paralysis (less than 1) but was not completely well.

For the dual fluorescence analysis shown in FIGS. 1 and 2, the antibodies used were the RT7.2-PE Ab (Pharmingen, La Jolla, Calif.) and the MRC OX-40-FITC Ab (Pharmingen, La Jolla, Calif.). All the analysis was performed on a FACScan with the FACScan Research Software Version A (Becton Dickenson, San Jose, Calif.) operated according to the manufacturer's instructions.

Antigen Specific Proliferation Assays

Proliferation assays were performed in 96-well plates as described previously (Vandenbark, A. A. et al., 1985). Briefly, $2 \times 10^4$ CD4+ T-cells and $1 \times 10^6$ irradiated thymocytes/well were incubated in RPMI and 1% rat serum along with antigen and varying concentrations of the OX-40 immunotoxin or the toxin alone in a 200 μl volume. The cultures were incubated for 72 hr, the last 18 hr in the presence of 0.5 Bq [$^3$H]-thymidine. The cells were harvested onto glass fiber filters and [$^3$H]-thymidine uptake was assessed by liquid scintillation. Mean cpm were calculated from triplicate wells. The SD from replicate wells varied <10% from the mean values.

OX-40 Immunotoxin Inhibition of EAE

Naive Lewis rats were injected with an encephalitogenic dose of MBP specific CD4+ T-cells injected in one flank and injected with the immunotoxin at the same time in the opposite flank. Originally a dose curve for the immunotoxin was set up and the optimal dose was found to be between 300–500 μg/8 week old rat. As controls the same molar amount of the toxin alone (dgA) was given to animals in parallel.

Experimental Results

One of the keys to understanding the mechanism(s) by which autoantigen specific T-cells destroy self-tissue is to study the differences associated with an autoreactive T-cell at the site of inflammation versus a non-inflammatory site. To this end an experimental model system was set up in EAE to detect the cells that cause the disease in vivo.

EAE can be induced by the adoptive transfer of in vitro-activated MBP specific CD4+ T-cells into naive recipient rats. Four days after the transfer the animals start showing the paralytic signs of EAE. To allow detection of the donor population within the host, MBP specific F1 (Lewis×Buffalo) CD4+ T-cells were transferred into naive irradiated Lewis recipients. Lewis and Buffalo rats express allelic variants of an epitope of the CD45 cell surface molecule. These allelic variants are termed RT7.1 (Lewis) and RT 7.2 (Buffalo). The RT7.2 allelic marker can therefore be used to detect the F1 T-cells in Lewis hosts because these cells express both forms of the allele while Lewis rats only express the RT7.1 form of the allele. The CD45 molecule is expressed only on leukocytes and constitutes approximately 10% of the total surface protein.

FIG. 1 shows that on the first day of disease onset 50% of the MBP specific transferred population ($RT7.2^F$) wasposi-tive for the activation marker OX-40 at the site of inflammation (spinal cord), but the transferred population was negative for this cell surface antigen at the non-inflammatory sites (blood and spleen). This suggested that the OX-40 antigen was expressed on the cell surface of autoreactive CD4+ T-cells upon antigen recognition in vivo, because the MBP antigen is present on the T-cells in the spinal cord but not in the blood or spleen. The highest expression of the OX-40 antigen on the donor population isolated from the spinal cord was on the day before clinical signs of EAE and as the disease progressed this cell surface molecule went away (FIG. 2).

Figure 3:
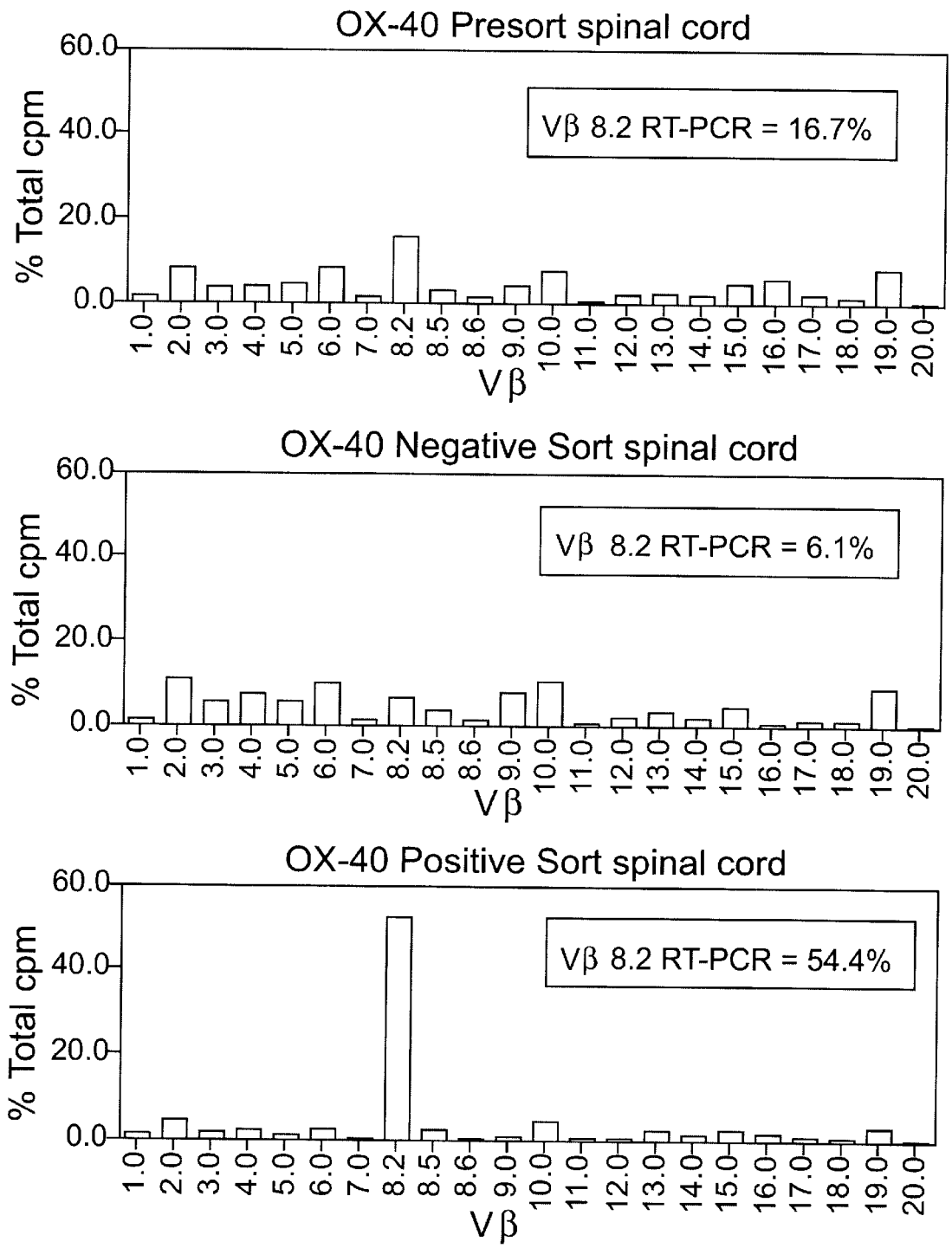
FIG. 3 shows TCR Vβ expression in OX-40 positive and negative sorted populations isolated from the spinal cords of Lewis rats with EAE. Lewis rats were actively immunised with myelin basic protein in CFA. Spinal cord lymphocytes were isolated at the onset of disease. The cells were immediately lysed after the OX-40 separation, the RNA was isolated, and analysed for Vβ T cell receptor gene usage. In the bottom two panels the cells were sorted with the FACStar (Becton-Dickenson, San Jose, Calif.), while the top panel compares the unsorted population. The unsorted cell population was stained with the Vβ8.2-FITC antibody and showed a similar positive percentage as observed with the PCR data in panel A.
Figure 4:
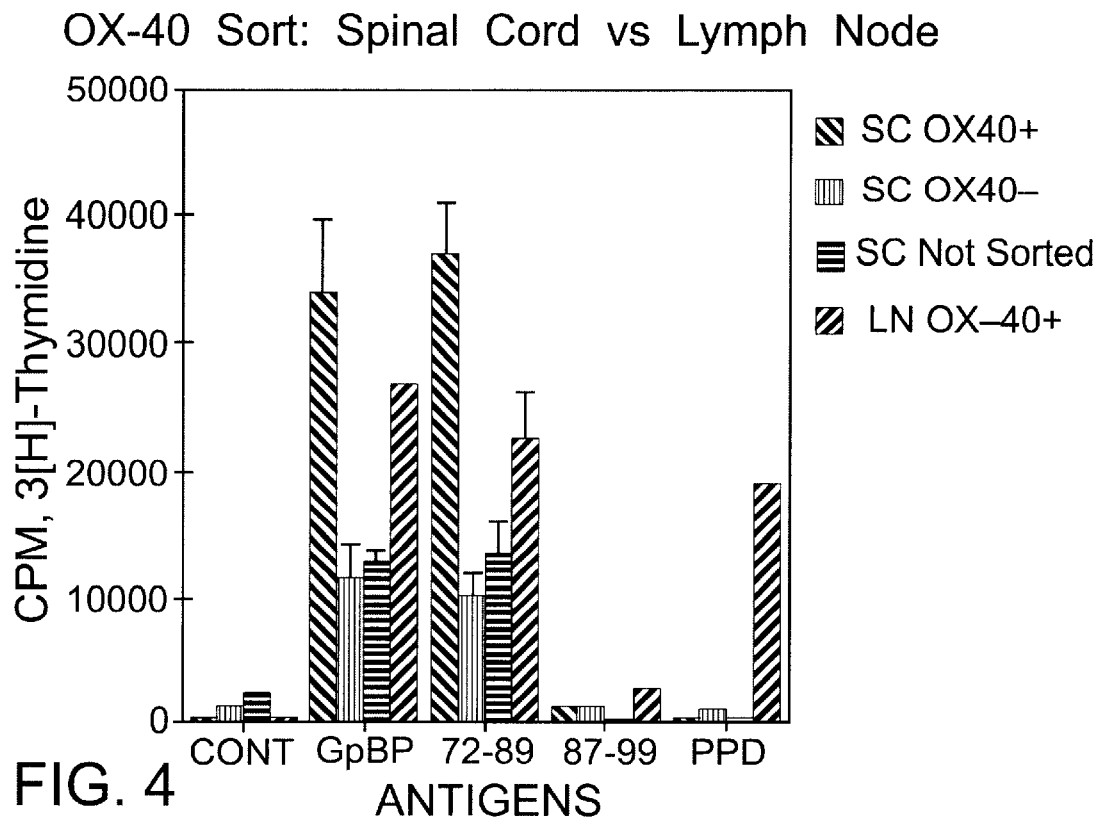
FIG. 4 shows antigen response to OX-40 positive cells isolated from the spinal cord and lymph node. Lewis rats were actively immunised with MBP in CFA and the spinal cord lymphocytes and lymph node cells were isolated at the onset of EAE. The cells were sorted into $OX-40^+$ and $OX-40^-$ fractions, cultured in IL-2 for 5 days, and were stimulated with the corresponding antigen. The unsorted spinal cord population was cultured in IL-2 for 5 days and assayed directly. The cells were incubated with irradiated thymocytes (APC) and antigen and 3[H]-Thymidine was added 48 hr later. Triplicate wells were harvested onto glass fiber filters 18 hr after the label was added. All of the cell types (except the unsorted population) were stimulated with Con A as a control and showed approximately 100,000 CPMs for each group (data not shown).

The Vβ8.2 T cell receptor (TCR) component is believed to be the predominant Vβ gene product associated with antigen specific CD4+ T cell response to the major encephalitogenic epitope of myelin basic protein (MBP) in Lewis rats. Lewis rats were actively immunised with MBP, and OX-40 positive and negative cells, were analysed for antigen reactivity and TCR Vβ utilisation (FIGS. 3 and 4). Sorted OX-40+ T cells isolated from the spinal cord were highly enriched for expression of the Vβ8.2 T cell receptor component compared to the OX-40− or unsorted spinal cord populations (see FIG. 3). FIG. 4 shows that whereas both MBP and PPD reactive T cells showed enriched responses in the OX-40+ fraction of the draining lymph node, only MBP reactive T cells were found in the OX-40+ fraction in the inflamed CNS. These data demonstrate the selective ability of the OX-40 antibody to mark the autoantigen reactive pathogenic T cells within the affected target organ in EAE. These data strongly suggest that Ag specific T cells can be isolated and characterised at the site of inflammation with the OX-40 antibody, thereby diagnosing the cell type directly involved with inflammation caused by autoantigen recognition. The data also imply that isolation of OX-40+ cells will be useful in identifying Vβ biases and autoantigen specific cells within inflamed tissues even when the antigen specificity is unknown.

Therefore, the OX-40 antigen is shown to be expressed ex vivo on antigen activated CD4+ T-cells and, furthermore, this antigen is shown to be exclusively expressed on the cells at inflammatory sites where the antigen is present (OX-40 is not expressed on cells at non-inflammatory sites in the absence of antigen). These results (the transient nature and target organ expression of the OX-40 marker) suggested that OX-40 may be a diagnostic marker and a suitable target for antibody mediated deletion of activated autoimmune CD4+ T-cells.

The deletion of selective subsets of lymphocytes can be mediated by antibodies or other binding proteins in vivo. This can be done either by choosing an antibody or other binding molecule which upon binding to cells expressing OX-40 will then activate other effector cells or proteins of the immune system to destroy the targetted cells: examples of this include lysis of cells via activation of the complement cascade or via triggering of antibody-dependent cellular cytotoxicity (ADCC) (see Hale et al 1983, Blood 62: 873–82: Greenwood et al 1993, Eur. J. Immunology 23: 1098–1104); or by modifying the antibody or binding molecule such that a toxic agent is attached which will kill the cell upon binding and ingestion.

It is possible to modify binding proteins, monoclonal antibodies or fragments thereof by a variety of means. For instance, it is possible by means of standard molecular biological techniques to construct a cDNA encoding a fusion protein part of which is a toxin (eg see Williams et al 1987, Protein Engineering 1: 493–98).

Alternatively, one can couple toxins, drugs or other molecules to proteins by standard chemical coupling procedures such as via thioether bonds (Glennie et al 1987, J. Immunology 139: 2367).

Several groups have shown that antibodies linked to toxic molecules (termed immunotoxins) can deplete cell populations expressing the appropriate antigen (Fulton, R. J., et al. 1988). The advantage of immunotoxins is that they are highly selective in their target cell specificity and that small doses can eliminate unwanted/potentially harmful cells.

A variety of cytotoxins can be used to produce immunotoxins. Ricin A chain-antibody conjugates have been used to delete both normal and neoplastic lymphocytes in vivo and in vitro (Fulton, R. J. et al., 1988; Street, N. E. et al., 1987). Other toxins such as Pseudomonas exotoxin A and diphtheria toxin have also been conjugated to antibodies and used to kill specific populations of cells (May, R. D., and Fulton, R. J. 1992).

In the late 1980s and early '90s several human Phase I/II clinical trials were performed using antibodies conjugated to the Ricin A chain (Weiner, L. M., et al.1989; Spliter, L. E., et al., 1987; Vitetta, E. S., et al., 1991). Most of the trials have involved using antibodies specific for cancer antigens in order to lower the tumor burden in cancer patients. Recently, there has been a development of "second generation" immunotoxins which have avoided some of the problems of non-specific immunogenicity and toxicity in the treated patients. This strategy uses the deglycosylated form of the Ricin A (dgA) chain conjugated to the tumor specific antibody. One such Phase I study used this modified form of the immunotoxin against B cell lymphomas in 15 patients (Vitetta, E. S., et. al., 1991). Approximately 40% of the patients achieved partial remissions in which their overall tumor burden was reduced by 50% or more. Killing of the tumor cells was rapid occurring within 1 week after completion of the therapy.

All of the in vivo studies presented herein use an OX-40 antibody-dgA conjugate. The antibody ricin. A conjugation was performed with a heterobifunctional cross-linker SPDP or SMPT by the method described by May, R. D. and Fulton, R. J. (1992). Briefly, a free amino group on the OX-40 antibody was reacted with the crosslinker and the macromolecule was purified. The purified OX-40 antibody product was then reacted with reduced ricin A chain (which has one free cysteine) and the hybrid molecule was purified.

Figure 5:
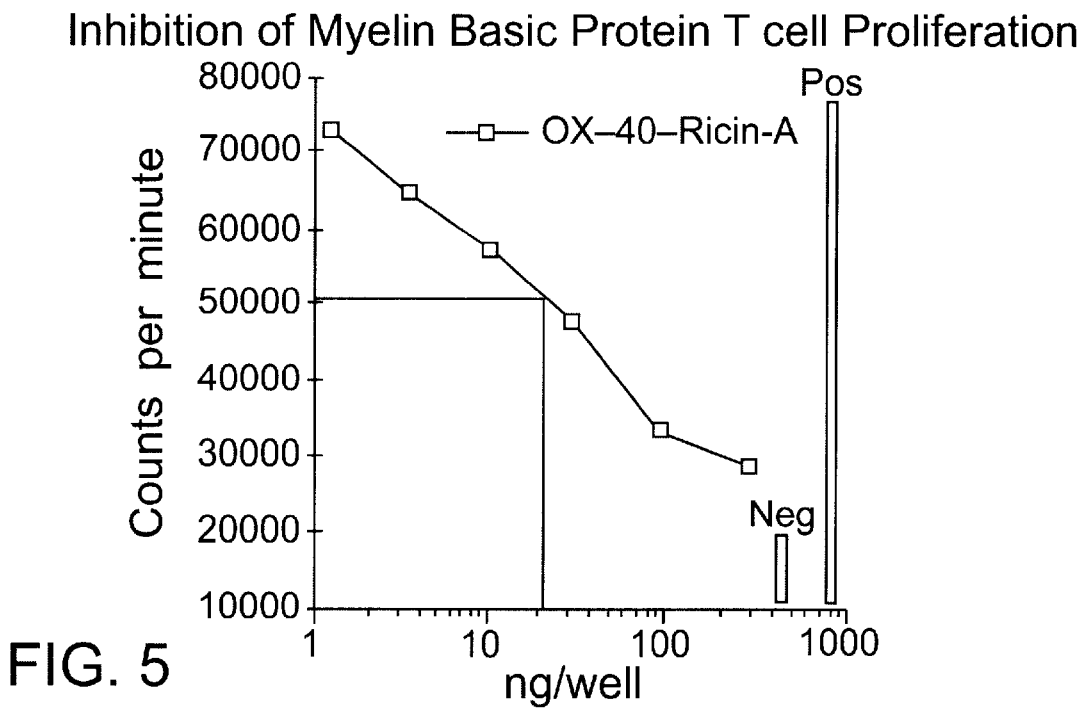
FIG. 5 is a graph showing dose dependent inhibition of antigen specific $CD4^+$ T-cell proliferation by the OX-40-dgA conjugate. Varying concentrations of the OX-40 immunotoxin was added to a constant amount of F1 T-cells, antigen presenting cells (APC), and MBP (myelin basic protein antigen). The open bars (to the right of the graph) show the proliferation (represented by [$^3$H]-thymidine incorporation) of these T-cells with and without antigen with no immunotoxin added (Pos and Neg respectively). The assay was carried out in a 200 µl volume.

Initially the rat OX-40 antibody was conjugated to the dgA form of Ricin and this heteroconjugate was used to inhibit the in vitro proliferation of antigen specific CD4+ T-cell lines. The T-cell lines used were specific for MBP and upon adoptive transfer caused EAE in naive recipients. FIG. 5 shows that the OX-40 heteroconjugate inhibited antigen specific proliferation of the MBP specific T-cell line in a dose dependent manner with 50% inhibition at approximately 20 ng/well. A control using Ricin A alone showed inhibition of the assay only at high concentrations 500 ng/well and above, but no effect on the assay at lower concentrations (data not shown). Controls using the OX-40 antibody alone and an isotype-matched unrelated antibody conjugated to dgA also showed no inhibition (data not shown).

Figures 6A, 6B:
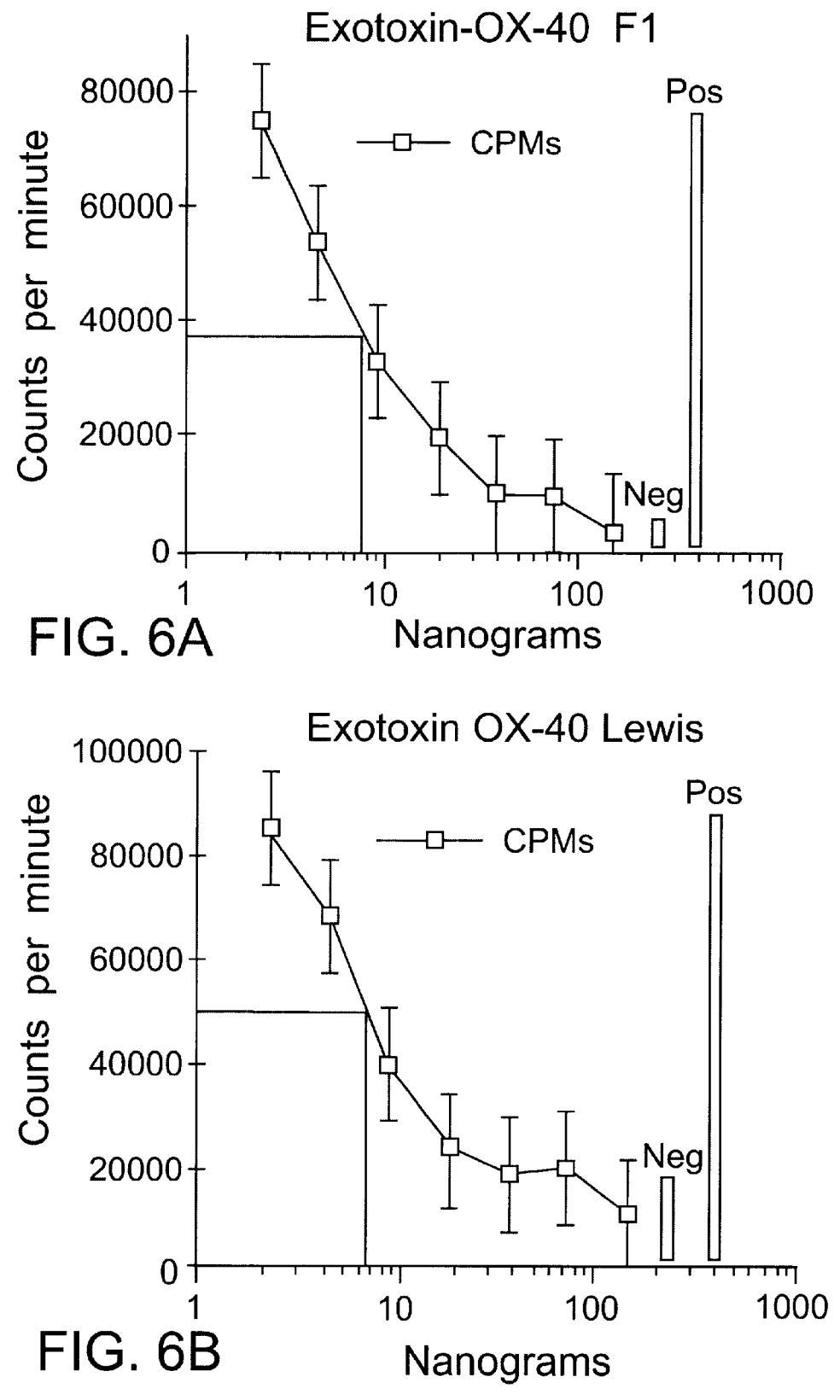

The OX-40 antibody was then conjugated to the Pseudomonas exotoxin and this conjugate was tested for inhibitory effect on antigen specific (MBP) CD4+ T-cell proliferation (FIGS. 6A–6B). This heteroconjugate was approximately 4-fold more efficient at inhibiting the in vitro assay, and the toxin alone did not inhibit the assay at any concentration. This assay was performed with a Lewis MBP specific line (FIG. 6B) and an F1 (Lewis×Buffalo) MBP specific line (FIG. 6A) with the same results, showing that the inhibition of proliferation was not strain specific.

Figure 7:
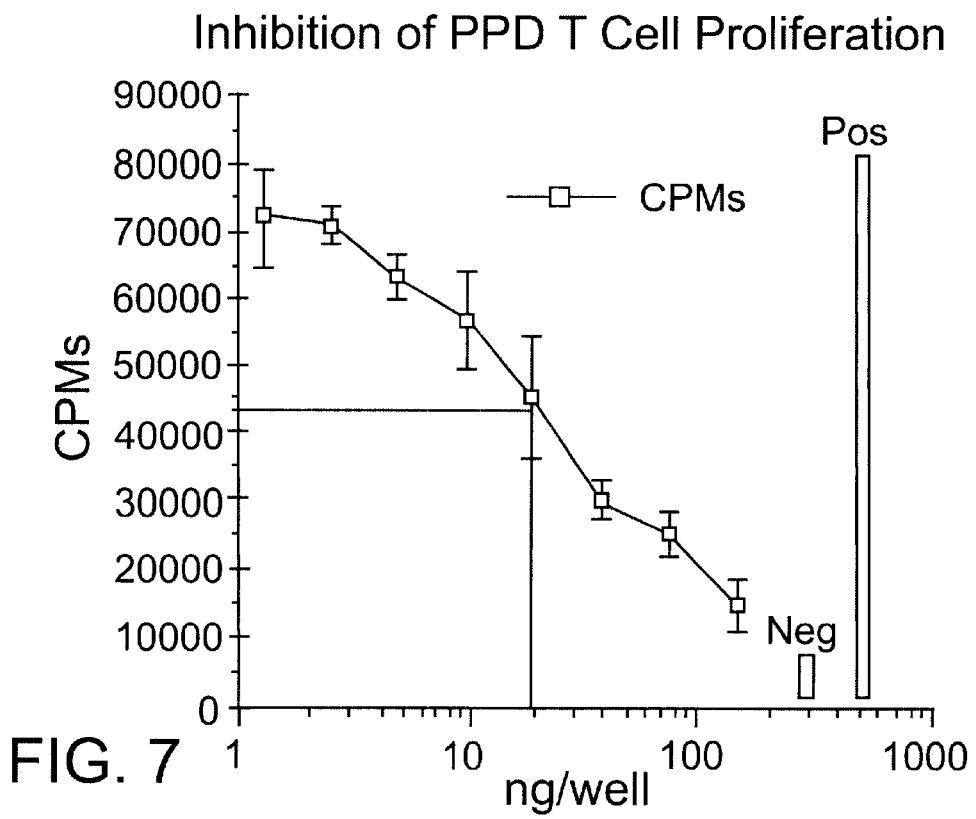
FIG. 7 is a graph showing dose dependent inhibition of PPD antigen specific CD4$^+$ T-cell proliferation by the OX-40-dgA conjugate. Varying concentrations of the OX-40 immunotoxin was added to a constant amount of F1 T-cells, antigen presenting cells (APC), and PPD (antigen). The open bars (to the right of the graph) show the proliferation (represented by [$^3$H]-thymidine incorporation) of these T-cells with and without antigen (Pos and Neg respectively). The assay was carried out in a 200 µl volume.

The OX-40-dgA was also used to inhibit the in vitro proliferation of a CD4+ T-cell line activated with an antigen that was irrelevant to EAE or autoimmunity. The antigen used was the purified protein derivative (PPD) antigen from *Mycobacterium tuberculosis*. This antigen was used to ascertain whether the OX-40 antigen was specific to CD4+ T-cells activated by the MBP antigen, or whether it is present on the surface of all antigen activated CD4+ T-cells regardless of T-cell receptor specificity. As shown in FIG. 7, there was a dose dependent inhibition of proliferation of the PPD activated T-cell line with a comparable 50% inhibition to the MBP activated lines. This shows that the OX-40 immunotoxin will inhibit proliferation of any activated CD4+ T-cell line regardless of the antigen specificity.

Since the OX-40 immunotoxin was effective at inhibiting the proliferation of MBP specific autoimmune CD4+ T-cells in vitro, experiments were then performed to determine the potential of this immunotoxin to kill MBP specific CD4+ T-cells in vivo. To this end irradiated rats were used initially; these animals received an encephalitogenic dose of MBP specific F1 T-cells. At the same time the animals were injected with the OX-4.0-Ricin A conjugate or Ricin Abalone. The effect of irradiation is to deplete the rat's immune system so that it would not recognize and deplete the allelic variant F1 donor T-cells. The use of irradiated rats facilitates the detection of the donor T-cells with the RT7.2 antibody in the host after the transfer of these cells and allows the fate of these transferred cells to be determined (see FIGS. 1, 2, 8A and 8B).

As shown in Table I, experiments 1 and 2, only 1/8 animals receiving the OX-40 immunotoxin showed clinical signs of disease while all 8 animals that received unconjugated Ricin A came down with EAE. The inhibitory effect of the immunotoxin appeared to be mediated by the OX-40 antibody since the Ricin A chain alone showed the same disease score when compared to animals injected with encephalitogenic CD4+ T-cells alone (data not shown).

TABLE I

OX-40 Ricin A Immunotoxin Effect on Experimental Autoimmune Encephalomyelitis

| Transfer Dose[a] | Treatment[b] | Incidence | Day of Onset | EAE Score[c] |
|---|---|---|---|---|
| Exp 1 | | | | |
| $6.5 \times 10^6$ | OX-40-Ricin A | 1/3 | 6 | 0.66 |
| $6.5 \times 10^6$ | Ricin A | 3/3 | 4 | 6.33 |
| Exp 2 | | | | |
| $10 \times 10^6$ | OX-40-Ricin A | 0/5 | — | — |
| $10 \times 10^6$ | Ricin A | 5/5 | 5 | 4.90 |
| Exp 3 | | | | |
| $10 \times 10^6$ | OX-40-Ricin A | 0/2 | — | — |
| $10 \times 10^6$ | No treatment | 3/3 | 4 | 6.50 |

[a]MBP specific CD4+ T-cells were stimulated for 3 days in vitro with antigen and antigen presenting cells and transferred into naive recipients.
[b]400 μg of OX-40-Ricin A or the same molar amount of Ricin A alone was injected at the same time the cells were transferred.
[c]Value represents the mean cumulative EAE score for each group. 0, no signs; 1, limp tail; 2, hind leg weakness; 3, hind quarter paralysis; 4, moribund.

Figure 8A:
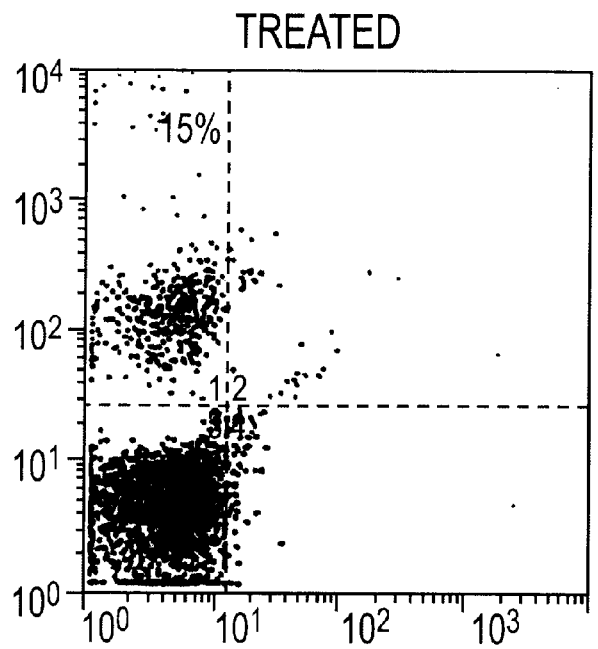
FIG. 8A and FIG. 8B are two dot plots from a FACS apparatus showing characterization of lymphocytes isolated from the spinal cord of rats that had been treated with a 400 µg dose of OX-40-dgA (FIG. 6A) or untreated rats (FIG. 6B). F1 MBP specific CD4$^+$ T-cells were transferred into irradiated Lewis recipients and OX-40-dgA was given on the same day of transfer. The transfer population was detected by the RT7.2 antibody conjugated to PE (represented on the y-axis) and counterstained with the control antibody anti-rat IgM-FITC.
Figure 8B:
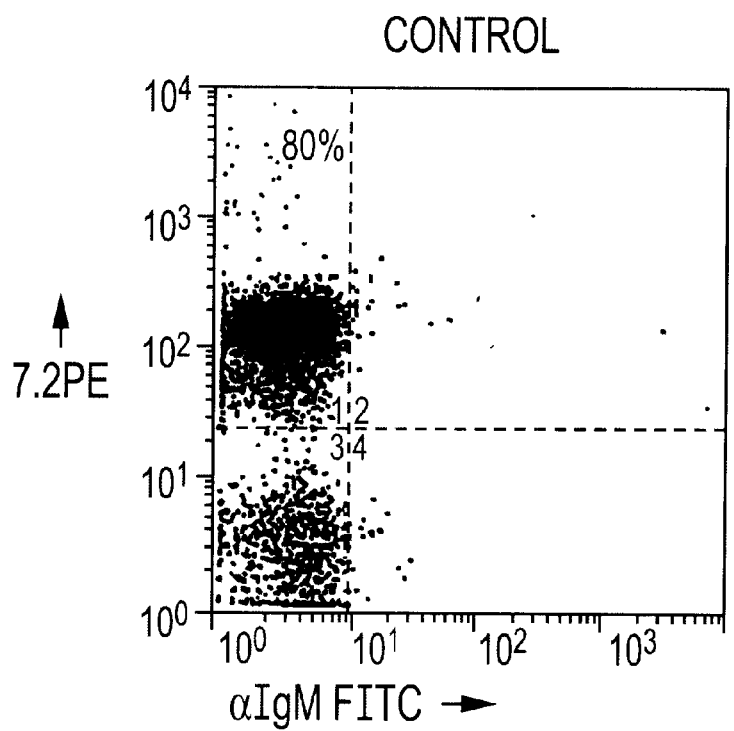

The data in Table I was generated using the EAE model where F1 MBP T-cell lines. (Lewis×Buffalo). were injected into irradiated Lewis (parental host) recipients. Thus, the transferred T-cell population could be detected in the spinal cord of these animals with the RT7.2 (Buffalo) antibody. FIGS. 8A and 8B show the outcome of the OX-40-dgA treatment as assessed by the number of donor cells isolated from the spinal cord of the treated (clinically well) and control groups (paralyzed) on the first day of disease onset. A total of 200,000 spinal cord lymphocytes was isolated from the control group and 80% were found to be donor derived. In contrast 80,000 spinal cord lymphocytes was isolated from the treated group and only 15% were found to be donor derived. There was over a log-fold difference in the total amount of donor derived MBP reactive CD4+ T-cells isolated from the spinal cord (the inflammatory site) between. the two groups (160,000 vs. 12,000). This suggested that OX-4.0 dGA conjugate was specifically deleting the MBP-reactive CD4+ T-cells in vivo.

Figure 9:
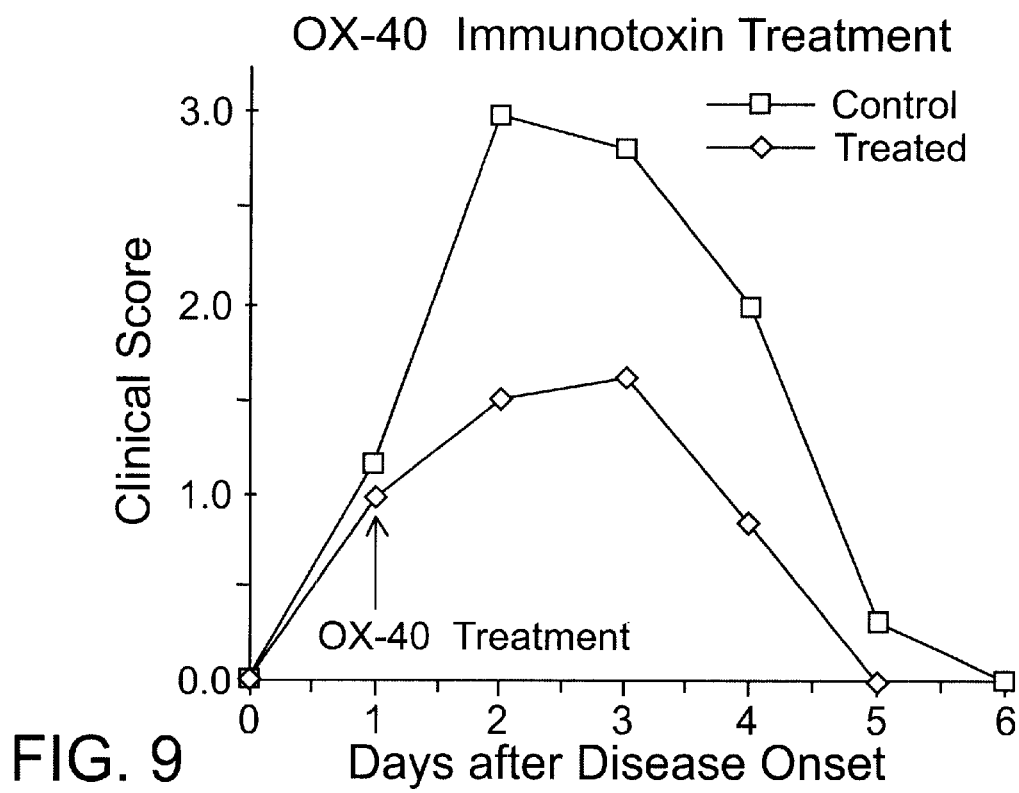
FIG. 9 shows OX-40 immunotoxin treatment administered on the first day of disease onset. F1 MBP specific T cells were transferred into 8 irradiated Lewis rats. On the first day of disease onset 4 of the animals were treated with 400 µg of OX-40 immunotoxin and were compared to the untreated "Control" animals. After treatment, both groups were scored daily until the clinical signs of EAE subsided. Each point on the graph represents the mean clinical score of 4 animals for the treated and control groups. The clinical scores were treated on the same scale as described in previous figures.

As shown in FIG. 9, animals were treated with OX-40 immunotoxin on the first day of disease onset when both groups had an average clinical score of 1. The day after treatment all the control animals showed signs of complete hind limb paralysis (score=3), while the treated animals progressed only slightly (score=1.5). The mean cumulative score after treatment was 8.0 in the control group and 3.75 in the treated group.

In a separate experiment, animals were treated on the first day of disease, and were sacrificed 24 hr later. The lymphocytes were then isolated from the spleens and spinal cords. Three groups were analysed for in vivo labelling of the OX-40 antibody. The controls received no treatment, the second group received unconjugated OX-40, and the third group received the OX-40 immunotoxin. Similar number of cells were recovered from the spleens, but half the amount of spinal cord lymphocytes were recovered from the OX-40 immunotoxin-treated animals compared to the control and the unconjugated OX-40-treated groups. In vivo binding of the OX-40 antibody was detected with an anti-mouse Ig-FITC. Approximately 15–20% of the lymphocytes isolated from the spinal cords of OX-40 and OX-40 immunotoxin treated rats were anti-mouse Ig positive. Cells isolated from the spinal cords of control rats were mouse Ig negative, even though 18% of the lymphocytes were OX-40 positive (Table Ia). There were very few anti-mouse Ig-FITC positive cells isolated from the spleens in any of the groups. A similar percentage of OX-40+ cells and anti-mouse Ig+ cells were isolated from the spinal cord of the OX-40 and OX-40 immunotoxin groups. The majority of anti-mouse Ig positive cells were associated with the donor population isolated from the spinal cord (RT7.2+/anti-mouse Ig+; Table Ia). These results dembnstrate that the in vivo administration of the OX-40 antibody resulted in the exclusive binding of autoantigen specific cells isolated from the inflamed tissue.

TABLE Ia

In Vivo Labelling of OX-40 Positive T Cells

| Treatment[a] Cell Isolation | OX-40+ | α-mouse Ig+ | Donor+/ Donor+ | α-mouse Ig+ |
|---|---|---|---|---|
| Control | | | | |
| Spinal Cord | 17.9%[b] | 0.2% | 54.4% | 0.3% |
| Spleen | 0.5% | 0.3% | 2.4% | 0.2% |
| OX-40 | | | | |
| Spinal Cord | 17.7% | 17.5%[c] | 53.2% | 13.5% |
| Spleen | 0.3% | 0.4% | 4.6% | 0.3% |
| OX-40-Ricin A[d] | | | | |
| Spinal Cord | 19.0% | 18.1% | 50.3% | 18.0% |
| Spleen | 0.7% | 0.5% | 2.3% | 0.4% |

[a]F1 T cells specific for MBP were transferred into irradiated Lewis hosts and 400 μg of OX-40 immunotoxin or OX-40 ab alone was administered i.p. the day of disease onset.
[b]All of the percent positive cells were determined by FACs analysis using isotype control antibodies to draw quadrants for negative comparisons.
[c]The mean fluorescence intensity (MFI) of the α-mouse Ig+ cells was very similar to MFI of the OX-40 FITC stained cells.
[d]The total number of spinal cord lymphocytes isolated from the OX-40 immunotoxin animals was half that of the OX-40 and the control groups.

Figure 10:
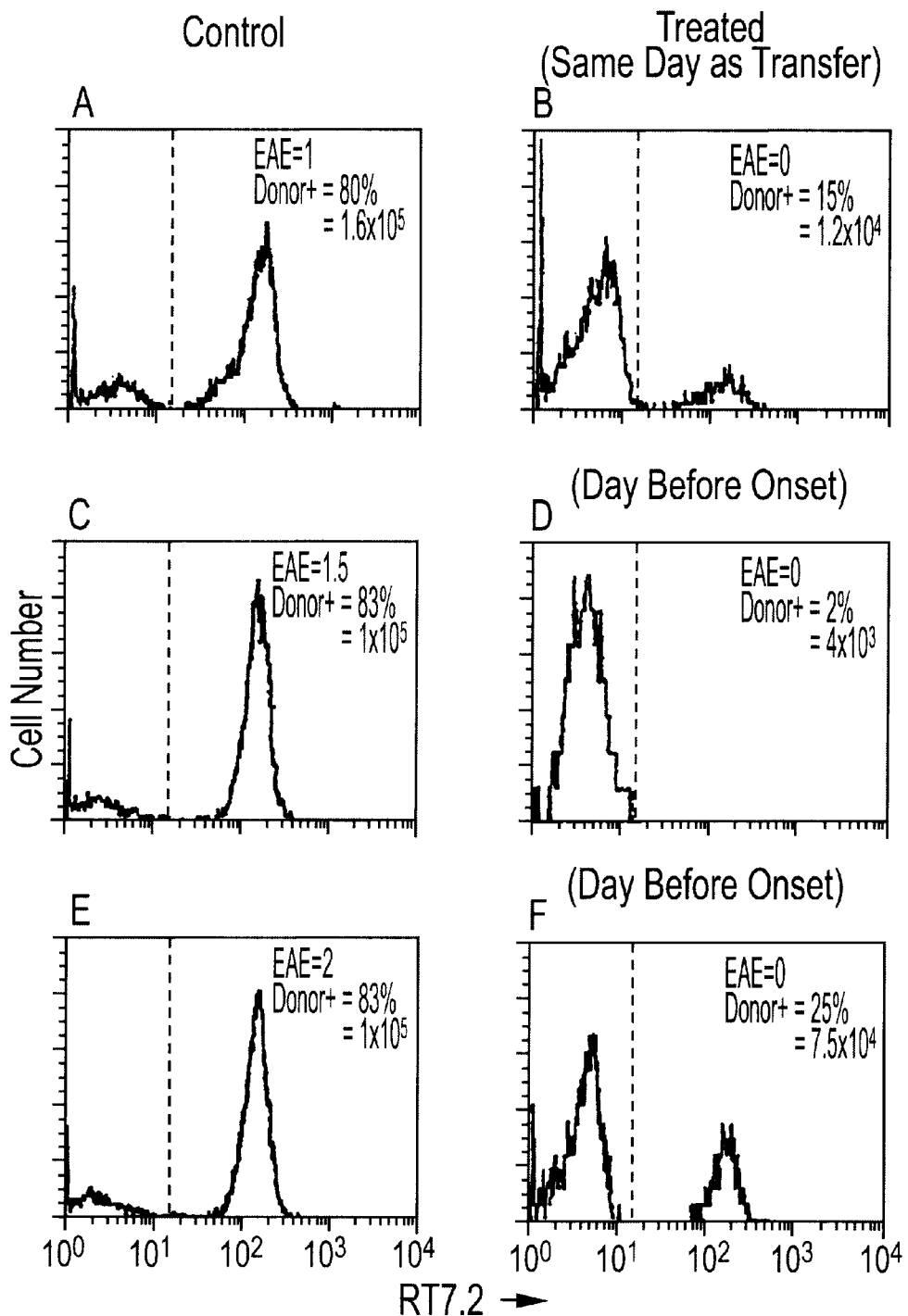
FIG. 10 shows effect on donor positive (MBP specific) T cells isolated from the spinal cord of animals treated with OX-40 immunotoxin. Irradiated Lewis rats were injected with F1 (Lewis×Buffalo) MBP specific T cells (1×10$^7$ cells/animal). In panels A, C, and E the animals were used as "controls" and received encephalitogenic cells alone. In panels B, D, and F the animals received encephalitogenic cells plus a single dose of OX-40 immunotoxin i.p. (400 µg/animal). Panel B shows the effect of the treatment given on the same day of cell transfer, while panels D and F show the effect of treatment given the day before disease onset (4 days after cell transfer). All the animals were sacrificed on the first day of disease onset which was 24 hr after treatment in panels D and F. The spinal cord lymphocytes were then stained with RT7.2-PE and the percent positive cells are shown in the top right corner. The total number of RT7.2$^+$ spinal cord lymphocytes are also shown and was calculated by multiplying the percentage of RT7.2$^+$ cells by the total number of lymphocytes isolated from the spinal cord prep. The EAE clinical score is represented in the top left corner and were the animals were rated according to the following scale: 0, no signs; 1, limp tail; 2, hind leg weakness, ataxia; 3, hind quarter paralysis; 4, front and hind limb paralysis, moribund condition. In this scale a half step (0.5) means the animals were in between the severity of the numbered scale.

In order to assess the efficacy of the treatment we isolated spinal cord lymphocytes and analysed the amount of BP reactive donor cells with the RT7.2 antibody from OX-40 immunotoxin treated rats versus control rats (F1 donor cells transferred into irradiated Lewis recipients). FIGS. 10A and 10B show the outcome of OX-40 immunotoxin administered on the same day of cell transfer as assessed by the number of myelin reactive donor T cells isolated from the spinal cord. RT7.2-positive cells were analysed the first day of disease onset; the treated animal was clinically well (EAE score=0, with $1.2\times10^4$ donor$^+$ spinal cord lymphocytes) while the control animal was paralysed (EAE score=1, with $1.6\times10^5$ donor$^+$ spinal cord lymphocytes). In FIGS. 10C, D, E and F the treatment was given the day before disease onset, when the only OX-40 positive donor T cells isolated from the rats were from the spinal cord (FIG. 1). Spinal cord and spleen lymphocytes were isolated 24 hr after the treatment. The number of donor-derived spleen cells isolated from the recipients was unaffected by the treatment (data not shown). In all the comparisons the number of donor$^+$ cells isolated from the spinal cord was decreased by over a log in the treated animals (FIG. 10). These data demonstrate that the OX-40 immunotoxin specifically depleted MBP reactive donor cells in vivo, and as a consequence less encephalitogenic cells were isolated from the spinal cord of the treated animals.

The same in vivo experiments were then performed in a non-irradiated host; a Lewis MBP activated T-cell line was transferred into a Lewis host. The non-irradiated host was used because this host has an intact immune system more similar to human patients suffering from these same types of autoimmune diseases. In these experiments it was initially observed that a single injection of the conjugate at the time of transfer of T-cells only partially inhibited subsequent development of the disease. Therefore experiments were performed utilizing two injections at different times.

Three animals were injected on day 0 and day 3 and compared to 3 control animals (Table II). These results suggest that the immunotoxin was recognizing and killing the autoimmune T-cells at the site of inflammation on day 3 because, (1) the only donor T-cells expressing the OX-40 antigen on day 3 (the day before disease onset) were in the spinal cord compartment (FIG. 1) and (2) the highest percentage of OX-40 expression on donor T-cells in the spinal cord was the day before disease onset (FIG. 2).

TABLE II

OX-40-Ricin A Immunotoxin Effect on Experimental Autoimmune Encephalomyelitis (in non-irradiated host)

| Transfer Dose$^a$ | Treatment$^b$ | Days of Injection | Day of Onset | EAE Score$^c$ |
|---|---|---|---|---|
| $9.0 \times 10^6$ | OX-40-Ricin A | 0/3 | 5 | 1.33 |
| $9.0 \times 10^6$ | Nothing | — | 4 | 8.25 |

$^a$Lewis MBP specific CD4$^+$ T-cells were stimulated for 3 days in vitro with antigen and antigen presenting cells and transferred into Lewis recipients.
$^b$400 μg of OX-40-Ricin A or the same molar amount of Ricin A alone was injected at the same time the cells were transferred.
$^c$Value represents the mean cumulative EAE score for each group of 3 animals. 0, no signs; 1, limp tail; 2, hind leg weakness; 3, hind quarter paralysis; 4, moribund.

The conclusion from the data presented is that the OX-40 immunotoxin is extremely effective at killing/inhibiting antigen specific CD4$^+$ T-cell function both in vitro and in vivo. The effect of this specific immunotoxin does not seem to be restricted by strain or antigen specificity and will most likely have a wide range of applications in vivo.

The experiments described above were performed using the rat model system and antibodies against the rat OX-40 protein. However, the rat OX-40 antibody does not recognize human or murine activated CD4$^+$ T-cells (data not shown). To facilitate the development of the present invention for human therapeutic use, it is necessary to produce antibodies against the human OX-40 protein.

To that end, a human cDNA encoding the human OX-40 homolog was cloned. Initially, two oligonucleotide primers were synthesized for use in the polymerase chain reaction (PCR). These primers were designed to amplify the full length OX-40 cDNA sequence; one primer was homologous to the coding strand in the region of the start codon of the rat cDNA sequence and the other was the inverse complement of the coding strand in the region of the stop codon of the rat cDNA sequence. Surprisingly, no product was ever obtained when these PCR primers were used with RNA isolated from activated CD4$^+$ T lymphocytes from humans.

Since the standard method of cloning the human OX-40 cDNA was unsuccessful, an alternative approach was required. First, the PCR primers were successfully used to clone the murine OX-40 cDNA by PCR from RNA isolated from murine CD4$^+$ T-cells activated with Concanavalin A (data not shown). Then, the murine OX-40 cDNA was used to probe a cDNA lambda gt11 library from human activated T lymphocytes (No. HL10316 purchased from Clontech, Palo Alto, Calif.). Five similarly sized positive clones (1050–1200 bp) were obtained. These five recombinant lambda clones were subcloned into the Bluescript plasmid (Stratagene, La Jolla) and then sequenced on the 370A automated sequencer (Applied Biosystems, Pasadena Calif.). The sequenceof the human OX-40 cDNA is set forth in SEQ. ID No. 1 in the accompanying sequence listing and is shown in FIG. 11.

A comparison of the predicted amino acid sequence of the human OX-40 protein with peptide sequences in the Genbank database indicated a high degree of homology with the murine OX-40 and rat OX-40 sequences; the probabilities that the predicted amino acid sequence of the human OX-40 protein shown in Seq. I.D. No. 1 was not related to the murine or rat OX-40 amino acid sequences were predicted to be $3.4\times10^{-58}$ and $2.9\times10^{-56}$ respectively. The next most closely related peptide sequence gave a probability of $1.1\times10^{-11}$. Furthermore, a comparison of the homologies between the human and rat OX-40 cDNA and amino acid sequences over a 64 amino acid (192 base pair) region starting at amino acid 31 of the rat sequence revealed an amino acid homology of 62.5% and a nucleotide homology of 67.5%. All ten cysteine residues within this 64 amino acid stretch were conserved.

OX-40 Expression in GVHD

The expression of OX-40 on T-cells was studied in patients with graft versus host disease (GVHD).

Three patients who underwent allogeneic bone marrow transplantation came down with GVHD. The day of GVHD onset varied between the patients from 7–50 days after transplant. Table 3 shows a summary of OX-40 expression during the GVHD episode. All the patients showed an increased percentage of CD4$^+$ peripheral blood cells expressing OX-40 during the early stage of disease development. In all the patients the percentage of OX-40$^+$ T cells declined after the initial clinical episode (7–14 days post GVHD). This data is consistent with the transient expression of OX-40 observed during the early stages of disease development in EAE (FIG. 2). OX-40 expression in GVHD correlated with the early development of the clinical signs and may have direct diagnostic and therapeutic applications for this and other human transplant/autoimmune disorders.

TABLE 3

OX-40 Expression in PBLS of Bone Marrow Transplant Patients with Graft Versus Host Disease

| Patient | Days Post GVH | % CD4+ | % OX-40+ of CD4[a] | Severity[b] |
|---------|---------------|--------|--------------------|-------------|
| #1 | 3 | 5.8[c] | 24.0[c] | grade 4 |
|    | 7 | 5.0 | 0.5 | |
|    | 14 | 4.0 | 1.6 | |
| #2 | 1 | 12.1 | 10.5 | grade 2 |
|    | 10 | 6.6 | 0.5 | |
| #3 | 2 | 41.0 | 10.0 | grade 2 |
|    | 8 | 8.3 | 0.6 | |

[a]Donor and recipient peripheral blood lymphocytes were screened for OX-40 expression prior to the transplant process and the CD4+ T cells were less than 1% OX-40+.
[b]Value represents the maximum severity each patient obtained during clinical signs of GVHD (skin involvement). 0, no signs; 1 - greater than no involvement but involving <25% of skin; 2 - >25% involvement but <50% involvement; 3 - >50% involvement; 4 - >50% involvement with blisters; 5 - leading to death.
[c]Lymphocytes from the peripheral blood of GVHD patients were isolated by Hypaque-Ficoll. Samples were isolated and analysed at various days post GVH. The samples were dual stained with an anti-human CD4-PE antibody and an anti-human OX-40 antibody. The OX-40 antibody was detected with an anti-mouse IgG₁-FITC and the indirect antibody alone was used as the negative control.

OX40 and IBD

It has been found that OX-40 can be of use in connection with IBD.

The tissue expression of OX40 was investigated using the standard technique of indirect alkaline phosphatase immunohistochemical staining (see eg Immunbcytochemistry: Practical Applications in Pathology and,Biology. J. Polak and S. van Noorden, eds. John Wright and Sons, Bristol). Biopsy tissue samples of intestine from both ulcerative colitis and Crohn's disease patients stained positively with an anti-OX40 antibody. Clusters of OX40+ cells were seen among the lymphoid cells infiltrating the lamina propria at sites of inflammation. In samples of intestinal tissue from normals or in samples of uninvolved intestinal tissue from patients only isolated, scattered OX40+cells were seen.

EXAMPLE ONE

Having herein provided the sequence of the human OXT-40 cDNA, one skilled in the art will recognize that the full length cDNA clone can now readily be obtained by standard methods. Such methods include, for example, the polymerase chain reaction (PCR) by which means DNA sequences can be amplified. Methods and conditions for PCR amplification of DNA are described in Innis et al. (1990) and Sambrook et al. (1989).

The selection of PCR primers for amplification of the human OX-40 cDNA will be made according to the portions of the cDNA which are desired to be amplified. Primers may be chosen to amplify small fragments of the cDNA or the entire cDNA molecule. Variations in amplification conditions may be required to accommodate primers of differing lengths; such considerations are well known in the art and are discussed in Innis et al. (1990). By way of example only, the entire cDNA molecule corresponding to the human OX-40 cDNA may be amplified using the following primers. Primers 1 and 2 are also set forth in the accompanying sequence listing as SEQ I.D. Nos. 2 and 3, respectively.

Primer 1: 5' ATGTGCGTGGGGGCTCGGCGGCTG 3'

Primer 2: 5' TCAGAACTTGACCAGGGTGGAGTG 3'

Template DNA for PCR amplification to produce the human OX-40 cDNA can be extracted from the lambda GT11 cDNA library from human activated T lymphocytes produced by Clontech, Palo Alto, Calif. (Catalog No. HL10316).

Alternatively, the human OX-40 cDNA may be obtained by PCR amplification of reverse transcribed RNA (RT-PCR) (Veres et al., 1987; Kawasaki et al., 1990). Essentially, total RNA is extracted from activated human CD4 T-cells by any one of a variety of methods routinely used as described in Sambrook et al. (1989) and Ausubel et al. (1987). Suitable human CD4 T-cells include the human CD4+ T-cell lymphoma cell line described by Gootenberg et al. (1981). Alternatively, activated CD4+ T-cells can be isolated from human peripheral blood as described by Kruisbeek (1992). The extracted RNA is then used as a template for performing RT-PCR amplification of the human OX-40 cDNA.

Standard methods for the purification and cloning of PCR products are well known in the art and are described by Innis et al. (1990) and Sambrook et al. (1989).

EXAMPLE TWO

With the provision of the human OX-40 cDNA, the expression and purification of the human OX-40, protein by standard laboratory techniques is now enabled. The purified protein may be used for antibody production and patient therapy.

Partial or full-length cDNA sequences, which encode for the subject protein, may be ligated into bacterial expression vectors. Methods for expressing large amounts of protein from a cloned gene introduced into *Escherichia coli* (*E. coli*) may be utilized for the purification of the human OX-40 protein. For example, fusion proteins consisting of amino terminal peptides encoded by a portion of the *E. coli* lacZ or trpE gene linked to the part or all of the human OX-40 protein may be used to prepare polyclonal and monoclonal antibodies that recognize the human OX-40 protein. Intact, native proteins may also be produced in *E. coli* in large amounts for functional studies. Methods and plasmid vectors for producing fusion proteins and intact native proteins in bacteria are described in Sambrook et al. (1989) (ch. 17, herein incorporated by reference). Such fusion proteins may be made in large amounts, are easy to purify, and can be used to produce antibodies. Native proteins can be produced in bacteria by placing a strong, regulated promoter and an efficient ribosome binding site upstream of the cloned gene. If low levels of protein are produced, additional steps may be taken to increase protein production; if high levels of protein are produced, purification is relatively easy. Suitable methods are presented in Sambrook et al. (1989) and are well known in the art. Often, proteins expressed at high levels are found in insoluble inclusion bodies. Methods for extracting proteins from these aggregates are described by Sambrook et al. (1989) (ch. 17). Vector systems suitable for the expression of lacZ fusion genes include the pUR series of vectors (Ruther and Muller-Hill, 1983), pEX1–3 (Stanley and Luzid, 1984) and pMR100 (Gray et al., 1982). Vectors suitable for the production of intact native proteins include pKC30 (Shimatake and Rosenberg, 1981), pKK177-3 (Amann and Brosius, 1985) and pET-3 (Studiar and Moffatt, 1986). Human OX-40 fusion proteins may be isolated from protein gels, lyophilized, ground into a powder and used as antigen preparations.

For expression in mammalian cells, the cDNA sequence may be ligated to heterologous promoters, such as the simian virus (SV)40 promoter in the pSV2 vector (Mulligan and Berg, 1981), and introduced into cells, such as monkey COS-1 cells (Gluzman, 1981), to achieve transient or long-term expression. The cDNA sequence (or portions derived from it) or a mini gene (a cDNA with an intron and its own promoter) is introduced into eukaryotic expression vectors by conventional techniques. These vectors are designed to permit the transcription of the cDNA eukaryotic cells by providing regulatory sequences that initiate and enhance the transcription of the cDNA. Vectors containing the promoter and enhancer regions of the SV40 or long terminal repeat (LTR) of the Rous Sarcoma virus and polyadenylation and splicing signal from SV40 are readily available (Mulligan et al., 1981; Gorman et al., 1982). The level of expression of the cDNA can be manipulated with this type of vector, either by using promoters that have different activities (for example, the baculovirus pAC373 can express cDNAs at high levels in *S. frugiperda* cells (Summers and Smith, 1985)) or by using vectors that contain promoters amenable to modulation, for example, the glucocorticoid-responsive promoter from the mouse mammary tumor virus (Lee et al., 1982).

In addition, some vectors contain selectable markers such as the gpt (Mulligan and Berg, 1981) or neo (Southern and Berg, 1982) bacterial genes. These selectable markers permit selection of transfected cells that exhibit stable, long-term expression of the vectors (and therefore the cDNA). The vectors can be maintained in the cells as episomal, freely replicating entities by using regulatory elements of viruses such as papilloma (Sarver et al., 1981) or Epstein-Barr (Sugden et al., 1985). Alternatively, one can also produce cell lines that have integrated the vector into genomic DNA. Both of these types of cell lines produce the gene product on a continuous basis. One can also produce cell lines that have amplified the number of copies of the vector (and therefore of the cDNA as well) to create cell lines that can produce high levels of the gene product (Alt et al., 1978).

The transfer of DNA into eukaryotic, in particular human or other mammalian cells, is now a conventional technique. The vectors are introduced into the recipient cells as pure DNA (transfection) by, for example, precipitation with calcium phosphate (Graham and Vander Eb, 1973) or strontium phosphate (Brash et al., 1987), electroporation (Neumann et al., 1982), lipofection (Felgner et al., 1987), DEAE dextran (McCuthan et al., 1968), microinjection (Mueller et al., 1978), protoplast fusion (Schafner, 1980), or pellet guns (Klein et al., 1987). Alternatively, the cDNA can be introduced by infection with virus vectors. Systems are developed that use, for example, retroviruses (Bernstein et al., 1985), adenoviruses (Ahmad et al., 1986), or Herpes virus (Spaete et al., 1982).

The human OX-40 protein expressed in eukaryotic cells may be purified and used to produce antibodies. The human OX-40 protein may be extracted following release of the protein into the supernatant, or, the cDNA sequence may be incorporated into a eukaryotic expression vector and expressed as a chimeric protein with, for example, β-qlobin. Antibody to β-globin is thereafter used to purify the chimeric protein. Corresponding protease cleavage sites engineered between the β-globin gene and the cDNA are then used to separate the two polypeptide fragments from one another after translation. One useful expression vector for generating β-globin chimeric proteins is pSG5 (Stratagene, La Jolla, Calif.). This vector encodes rabbit β-globin.

This invention encompasses recombinant cloning vectors containing the human OX-40 cDNA sequence, or portions thereof. The human OX-40 cDNA is operatively linked in the vector to an expression control sequence in the recombinant DNA molecule so that the human OX-40 polypeptide, or a portion thereof, can be expressed. The expression control sequence may be selected from the group consisting of sequences that control the expression of genes of prokaryotic or eukaryotic cells and their viruses and combinations thereof. The expression control sequence may be specifically selected from the group consisting of the lac system, the trp system, the tac system, the trc system, major operator and promoter regions of phage lambda, the control region of fd coat protein, the early and late promoters of SV40, promoters derived from polyoma, adenovirus, retrovirus, baculovirus and simian virus, the promoter for 3-phosphoglycerate kinase, the promoters of yeast acid phosphatase, the promoter of the yeast alpha-mating factors and combinations thereof.

The host cell, which may be transfected with the vector of this invention, may be selected from the group consisting of *E. coli*, Pseudomonas, *Bacillus subtilis, Bacillus stearothermophilus* or other bacilli; other bacteria; yeast; fungi; insect; mouse or other tissue cells, including human tissue culture cells.

In a preferred embodiment of the present invention, the full length human OX-40 cDNA as shown in FIG. 9 (from start codon to stop codon) is ligated into a baculovirus vector and the recombinant human protein is produced in the appropriate insect cells. Suitable baculovirus expression systems include the BacPAK™ Baculovirus Expression System produced by Clontech (Palo Alto, Calif.). Thus, by way of example, the full length human OX-40 cDNA is ligated into the plasmid pBacPAK1 and expressed in *Spodoptera fugiperda* cells according to the manufacturer's instructions.

The human OX-40 protein produced in the insect cells is then purified by standard techniques. A preferred technique of isolating the recombinant product is to use a vector that adds an additional 6 residues of histidine to the recombinant protein. Fusion proteins produced in this manner chelate metal, which facilitates protein purification enormously. Thus, for example, in high salt, polyhistidine fusion proteins bind with a high affinity to a metal chelate matrix whereas the majority of host proteins do not bind at all. Low affinity binding host proteins can be washed off the matrix by decreasing the pH to 6.0. Specific elution of the polyhistidine-containing fusion protein can be accomplished with 300 mM imidazole buffer at pH 6.0.

EXAMPLE THREE

Monoclonal antibodies may be produced to the human OX-40 protein for therapeutic use. Substantially pure human OX-40 protein suitable for use as an immunogen is isolated from the transfected or transformed cells as described in Example 2 above. Concentration of protein in the final preparation is adjusted, for example, by concentration on an Amicon filter device, to the level of a few milligrams per milliliter. Monoclonal antibody to the protein can then be prepared as follows:

A. Monoclonal Antibody Production by Hybridoma Fusion.

Monoclonal antibody to epitopes of the human OX-40 protein identified and isolated as described can be prepared from murine hybridomas according to the classical method of Kohler and Milstein (1975) or derivative methods thereof. Briefly, a mouse is repetitively inoculated with a few micrograms of the selected purified protein over a period of a few weeks. The mouse is then sacrificed, and the antibody-producing cells of the spleen isolated. The spleen cells are fused by means of polyethylene glycol with mouse myeloma cells, and the excess unfused cells destroyed by growth of the system on selective media comprising aminopterin (HAT media). The successfully fused cells are diluted and aliquots of the dilution placed in wells of a microtiter plate where growth of the culture is continued. Antibody-producing clones are identified by detection of antibody in the supernatant fluid of the wells by immunoassay procedures, such as ELISA, as originally described by Engvall (1980), and derivative methods thereof. Selected positive clones can be expanded and their monoclonal antibody product harvested for use. Detailed procedures for monoclonal antibody production are described in Harlow and Lane (1988).

B. Antibodies Raised Against Synthetic Peptides.

An alternative approach to raising antibodies against the human OX-40 protein is to use synthetic peptides synthesized on a commercially available peptide synthesizer based upon the predicted amino acid sequence of the human OX-40 protein shown in FIG. 11.

In a preferred embodiment of the present invention, monoclonal antibodies that recognize the human OX-40 protein are produced. Optimally, monoclonal antibodies raised against the human OX-40 protein specifically detect the human OX-40 protein. That is, such antibodies recognize and bind the human OX-40 protein and do not substantially recognize or bind to other proteins found in human cells. Put another way, such antibodies have a specificity of binding in humans to substantially only the human OX-40 protein and thus to substantially only activated $CD4^+$ T-cells.

The determination that an antibody specifically detects the human OX-40 protein is made by any one of a number of standard immunoassay methods; for instance, the Western blotting technique (Sambrook et al., 1989). To determine that a given antibody preparation (such as one produced in a mouse) specifically detects the human OX-40 protein by Western blotting, total cellular protein is extracted from human cells that do not express the OX-40 antigen, such as non-activated lymphocytes. As a positive control, total cellular protein is also extracted from activated T-cells especially for example activated $CD4^+$ T-cells. These protein preparations are then electrophoresed on a sodium dodecyl sulfate-polyacrylamide gel. Thereafter, the proteins are transferred to a membrane (for example, nitrocellulose) by Western blotting, and the antibody preparation is incubated with the membrane. After washing the membrane to remove non-specifically bound antibodies, the presence of specifically bound antibodies is detected by the use of an anti-mouse antibody conjugated to an enzyme such as alkaline phosphatase; application of the substrate 5-bromo-4-chloro-3-indolyl phosphate/nitro blue tetrazolium results in the production of a dense blue compound by immuno-localized alkaline phosphatase. Antibodies which specifically detect the human OX-40 protein will, by this technique, be shown to bind to the human OX-40 protein band (which will be localized at a given position on the gel determined by its molecular weight). Non-specific binding of the antibody to other proteins may occur and may be detectable as a weak signal on the Western blot. The non-specific nature of this binding will be recognized by one skilled in the art by the weak signal obtained on the Western blot relative to the strong primary signal arising from the specific antibody-human OX-40 protein binding. Preferably, no antibody would be found to bind to proteins extracted from the unactivated T-cells especially for example $CD4^+$ T-cells.

In addition to binding assays using extracted proteins, monoclonal antibodies raised against the human OX-40 protein are tested to confirm their ability to recognize the appropriate cell type (activated human T-cells especially for example activated $CD4^+$ T-cells) by conjugating the human OX-40 antibody to a fluorescent tag (such as FITC) and analyzing cell populations by FACS as described above. The human OX-40 antibody will preferably recognize activated T-cells especially for example activated $CD4^+$ T-cells. Therefore, dual staining of an activated T-cell population with CD4-PE and OX-40-FITC should show cells that are double positive.

Monoclonal antibodies for use in the present invention will generally be of the IgM or IgG isotype, and will preferably be of mouse, human or other mammalian origin.

In one preferred embodiment of the present invention, the monoclonal antibodies that recognize the human OX-40 antigen are mouse monoclonal antibodies that have been "humanized". Such humanized antibodies can be more safely administered to human patients than can unmodified monoclonal antibodies produced in mouse cells. Monoclonal antibodies produced in non-human cells, such as mouse cells, generally evoke an immune response when administered to a human host, thus limiting the duration of the biological efficacy of the monoclonal antibody (see generally, U.S. Pat. No. 4,731,244 and WO 89/06976). Humanized antibodies are produced by recombinant DNA technology and generally comprise the antibody constant region from human monoclonal antibodies combined with the variable (antigen recognition) region from the mouse monoclonal antibody that recognizes the target antigen (in this case the human OX-40 protein). Because only the variable region is of murine origin, humanized monoclonal antibodies are significantly less likely to induce an immune response when administered to a human patient.

Methods for humanizing antibodies are described by Riechmann et al. (1988). Riechmann et al. introduced the six hypervariable regions from the heavy and light chain domains of a rat antibody into a human IgG1 antibody directed against human lymphocytes. Riechmann et al. showed that this "humanized" antibody was able to bind to its target antigen in vivo without eliciting an anti-immunoglobulin immune response.

For the preferred embodiments of this invention, intact monoclonal antibodies are used. However, one skilled in the art will recognize that portions of monoclonal antibodies that are capable of recognizing and binding to the human OX-40 protein may also be employed. These antibody fragments generally include Fab, $F(ab)'^2$ and Fv fragments of antibodies which recognize the human OX-40 protein. Immunotoxins comprising antibody fragments have been shown to be effective in deleting $CD4^+$ T-cells both in vivo and in vitro using an antibody that recognizes all cells that express the CD4 antigen (Street et al., 1987).

EXAMPLE FOUR

As set forth in the preceding examples, this invention enables the production of monoclonal antibodies that, in humans, bind substantially only the human OX-40 protein. Such monoclonal antibodies can be used in therapeutic applications, for example in the form of conjugates with cytotoxic molecules, e.g. as antibody-ricin-A conjugates as discussed below. Such conjugates are commonly referred to as immunotoxins. Immunotoxins are characterized by two components; an active moiety which is usually fatal to a cell when attached or absorbed, and a "delivery vehicle" which serves to deliver the cytotoxin to the target cell type. For the present invention, the target cell type is activated T-cells especially for example activated $CD4^+$ T-cells and the delivery vehicle is an antibody or antibody fragment that recognizes and binds to the human OX-40 antigen, as described in Example 8 below. Active moieties that can be conjugated to the antibody or antibody fragment to produce immunotoxins include cytotoxins and radionuclides. (See generally, Olsnes and Phil (1982), and Baldwin and Byers (1985)).

Examples of radionuclides suitable for producing immunotoxins ("radioimmunoconjugates") for diagnosis or therapy include radio-iodine I-123, I-125, and I-131; technetium Tc-99/Tc-99m; radio-indium such as In-111; radio-rhenium such as Re-186 or Re-188; radio-copper such as Cu-67; Yttrium-90; and Bismuth-212. Radiolabeling techniques and the production of radioimmunoconjugates are described in the following publications, which are incorporated herein by reference: EP 0 150 844; EP 0 300 431 and EP 0 329 481 (labelling with metal redionuclides); EP 0 336 678 (radiolabelled proteins); EP 0 279 417 (Tc-99m labelling); EP 0 237 150 (radionuclide-antibody coupling); WO 88/07986 (I-123 in cancer therapy); EP 0 028 092 (Tc-99m antibody labelling); and WO 81/02522 (tumor localization and therapy with labelled antibodies and antibody fragments).

Examples of cytotoxic substances, including cytotoxic proteins, that may be conjugated with antibodies to form immunotoxins include cytotoxic polypeptide chains of diphtheria toxin, the Pseudomonas exotoxin and ricin toxins (such as the Ricin A chain and the deglycosylated form of the Ricin A chain (dgA); cytotoxic anthracyclines; daunomycin in conjugated form; antibody enzyme conjugates in combination with prodrugs for the delivery of cytotoxic agents to tumor cells, e.g., alkaline phosphatase ("AP"), in conjunction with prodrug etoposide-4'-phosphate or 7-(2'-aminoethyl phosphate)-mitomycin; ribosomal inhibiting protein; human tumor necrosis factor (hTNF); wavelength-specific cytotoxic agents (hydro-monobenzo-porphyrins "green porphyrins" (Gp)); and mitotic inhibitors, such as methotrexate in conjugated form. The following publications, incorporated herein by reference, describe the production and use of antibody-cytotoxin conjugates: EP 0 238 147 (anthracycline immunotoxins); EP 0 302 473 (antibody-enzyme conjugates in combination with prodrugs); WO 89/10140 (cytotoxin-immunoconjugates); EP 0 256 471 (ribosomal inhibiting proteins); EP 0 276 121 (wavelength-specific cytotoxins); EP 0 299 467 (methotrexate conjugated to an antibody as a mitotic inhibitor); EP 0 269 188 (ricin A chain); WO 88/00837 (daunomycin); WO 85/03508 (diphtheria and ricin toxins); and EP 0 131 789 (hTNF). In one embodiment of the present invention, the cytotoxin is the deglycosylated form of the Ricin A chain, as described in U.S. Pat. No. 4,590,071.

A selected cytotoxin or radionuclide may be conjugated with an anti- human OX-40 antibody to produce an immunotoxin for use in the present invention. Antibodies may be conjugated with cytotoxins or radionuclides by a number of well known procedures, as generally described in Thorpe et al. (1982). For example, where the cytotoxic agent is a protein (such as the Ricin A chain) and the delivery vehicle is an intact monoclonal antibody, the linkage may be by way of heterobifunctional cross linkers, such as carbodiimide or gluteraldehyde. Preferred methods of producing immunotoxins using the deglycosylated Ricin A chain are provided in U.S. Pat. No. 4,590,071, and WO 89/06967, which are herein incorporated by reference.

Immunotoxins as provided by the present invention and produced as described above are subsequently tested to confirm their in vitro efficacy. Such in vitro testing is performed using human $CD4^+$ T-cells and the methods described above. For example, an immunotoxin produced according to the present invention (i.e. a cytotoxin conjugated to a monoclonal antibody that has been shown to be specific to the human OX-40 protein), is tested using in vitro inhibition studies on MBP specific $CD4^+$ T-cell lines from multiple sclerosis patients. Immunotoxins potentially suitable for use in human therapy are those capable of inhibiting the in vitro proliferation of such cells.

Since these immunotoxins are capable of inhibiting the in vitro proliferation of activated $Cb4^+$ T-cells from multiple sclerosis patients, they should be capable of inhibiting the proliferation of all activated $CD4^+$ T-cells, regardless of origin. This conclusion is supported by the evidence set forth above, where the rat Ox-40-dgA immunotoxin was shown to be effective against MPB activated rat $CD4^+$ T-cells and PPD activated rat $CD4^+$ T-cells. To confirm that the human OX-40 immunotoxin has this general activity, similar in vitro proliferation studies as described above may also be performed with human $CD4^+$ T-cells specific for other antigens (such as herpes simplex virus.)

In an alternative embodiment of the present invention described in Example 5 below, anti-human OX-40 antibodies can also be used to diagnose conditions mediated by activated T-cells especially for example activated $CD4^+$ T-cells. For such applications, it is preferable that the antibody is conjugated to a suitable chemical "tag" which facilitates detection of the antibody. Suitable molecules are well known in the art and include the fluorescent molecules fluorescein isothiocyanate (FITC) and R-phycoerythrin (PE) as utilized in the present invention. Other examples of suitable fluorescent materials include lanthanide chelate labels, e.g., europium Eu+3 and a polypyridine or phenanthroline chelating agent; and rhodamine dyes, e.g., rhodamine 123. Methods of using fluorescent labels and methods of producing immunoconjugates using fluorescent labels are described in the following publications which are herein incorporated by reference: EP 0 288 256 (Eu+3); EP 0 323 152 (rhodamine dyes); EP 0 267 049 (mithramycin, Hoechst 33342, sulfofluorescein diacetate, Nile red and rhodamine 123); EP 0 195 623 (fluorescent rare earth labels); EP 0 290 269 (fluorescent chelates of lanthanide metal ions); and EP 0 324 323 (lanthanide chelates).

EXAMPLE FIVE

In one embodiment of the present invention, monoclonal antibodies that specifically bind the human OX-40 protein are used to detect conditions mediated by activated T-cells especially for example activated $CD4^+$ T-cells. For such purposes, human OX-40 antibodies are conjugated with other molecules, such as fluorescent markers.

Biopsy samples are taken from inflamed tissue for analysis. One skilled in the art will recognize that the source of the biopsy sample will vary between different conditions. In the case of multiple sclerosis the lymphocytes will be isolated from the CSF, while in rheumatoid arthritis the lymphocytes will be isolated from the synovial fluid of inflamed joints. In the case of transplant rejection biopsies will be taken directly from the target organ during a rejection episode.

In a preferred embodiment, a biopsy sample taken from a patient will be fractioned into a lymphocyte fraction (by methods described earlier; see Materials and Methods). The purified lymphocytes will be stained with the OX-40-FITC antibody and the percentage of positive lymphocytes will be quantitated on a FACScan apparatus. This percentage will be compared with the percentage found in healthy individuals. Any statistically significant increase will provide an early indication of an inflammatory event and will lead to early diagnosis of autoimmune disorders.

EXAMPLE SIX

For therapeutic applications, such as treatment of autoimmune inflammations associated with multiple sclerosis, it is anticipated that the presence of activated T-cells especially for example activated CD4+ T-cells at the site of inflammation will be established before treatment is commenced. The presence of these cells can be established using the diagnostic methods described in Example 5 above. If the diagnostic test produces a result indicating the presence of activated T-cells especially for example activated CD4+ T-cells at the inflammatory site, then therapeutic application of the immunotoxin may be appropriate.

For therapeutic administration of the immunotoxins for treatment of conditions mediated by activated T-cells, especially for example activated CD4+ T-cells, standard published protocols that set forth treatment regimes using immunotoxins may be utilized. These include protocols described by Vitetta et al., 1991, and in WO89/06967. These documents are herein incorporated by reference.

In general, the method of treating a patient suffering from a condition mediated by antigen-activated T-cells especially for example activated CD4+ T-cells will comprise administering to the patient an effective amount of an antibody (or a portion of an antibody) conjugated with a cytotoxic agent wherein the antibody (or the portion of the antibody) recognizes and binds to the human OX-40antigen. As discussed above, antibodies and portions of antibodies conjugated with a cytotoxic agent are commonly referred to as immunotoxins. Effective amounts of these immunotoxins may generally be referred to as a suitable dose of an immunotoxin.

One skilled in the art will recognize that any dose of the immunotoxins greater than zero will have some effect on the activated CD4+ T-cell population in a patient. However, suitable doses are limited by the onset of adverse side effects of high doses of immunotoxin. As described in WO89/06967, for immunotoxins comprising a monoclonal antibody conjugated with the ricin A chain, suitable doses are in the range of 0.05–1.0 mg/kg daily for up to 14 days. As described by Vitetta et al. (1991), for immunotoxins comprising antibody fragments (such as the Fab' fragment) linked to the chemically deglycosylated ricin A chain, doses will preferably be in the range of 25–150 mg/m².

EXAMPLE SEVEN

One embodiment of the present invention is a kit containing monoclonal antibodies that recognize the human OX-40 antigen. Such a kit would comprise a container within which the monoclonal antibody is contained.

In one embodiment of such a kit, the kit would contain the monoclonal antibody in a form conjugated with a cytotoxin, such as dgA, whereby the kit could be used to treat patients suffering from a condition mediated by activated T-cells especially for example activated CD4+ T-cells. This antibody-cytotoxin conjugate would preferably be provided in a form suitable for administration to a patient by injection. Thus, the kit might contain the antibody-cytotoxin conjugate in a suspended form, such as suspended in a suitable pharmaceutical excipient. Alternatively, the conjugate could be in a solid form suitable for reconstitution.

In an alternative embodiment, the kit would contain the monoclonal antibody in a form suitable for diagnostic use, such as conjugated to a fluorescent marker. Such kits would be used in the detection of inflammatory conditions mediated by activated T-cells especially for example activated CD4+ T-cells.

The foregoing examples are illustrative of the present invention, but are not limiting. Numerous variations and modifications on the invention as set forth can be effected without departing from the spirit and scope of the present invention.

REFERENCES

Ahmad et al. (1986). *J. Virol.* 57:267.

Amann and Brosius (1985). *Gene* 40:183.

Alt et al. (1978). *J. Biol. Chem.* 253:1357.

Baldwin and Byers (Eds.) (1985). "Monoclonal Antibodies for Cancer Detection and Therapy," pp. 159–179; 224–266.

Bernstein et al. (1985). *Gen. Engr'g* 7:235.

Birkeland, M. L., and A. N. Barclay (1992). Abstract: *8th International Congress of Immunology* W-18(1):82.

Bourdette, D. N. et al. (1991). *J. Neurosci. Res.* 30:308–315.

Brash et al. (1987). *Mol. Cell Biol.* 7:2013.

Caspi, R. R. et al. (1988). *J. of Immunol.* 140:1490–1495.

Cobbold, S. P. et al. (1984). *Nature* 312:548–552.

Cush, J. J., and Lipsky, P. E. (1988). *Arthritis and Rheumatism* 31(10):1230–1238.

Engvall (1980). *Enzymol.* 70:419.

Felgner et al. (1987). *Proc. Natl. Acad. Sci USA* 84:7413.

Fulton, R. J. et al. (1988). *Cancer Research* 48:2626–2631.

Gluzman (1981). *Cell* 23:175–182.

Gootenberg, J. E. et al. (1981). *Journal of Experimental Medicine,* 154:1403–1418.

Graham and vander Eb (1973). *Virology* 52:466.

Gray et al. (1982). *Proc. Natl. Acad. Sci. USA* 79:6598.

Gorman et al. (1982). *Proc. Natl. Acad. Sci USA* 78:6777–6781.

Harlow and Lane (1988). *Antibodies A Laboratory Manual,* Cold Spring Harbor Laboratory, New York.

Innis et al. (Eds.) (1990). *PCR Protocals, A Guide to Methods and Applications,* Academic Press, Inc., San Diego, Calif.

Klein et al. (1987). *Nature* 327:70.

Kohler and Milstein (1975). *Nature* 256:495.

Kawasaki et al. (1990). In *PCR Protocols, A Guide to Methods and Applications,* Innis et al. (eds.), 21–27, Academic Press, Inc. San Diego, Calif.

Kruisbeek, A. M. (1992). *Current Protocols in Immunology* (J. E. Coligan, A. M. Kruisbeek, D. H. Margulies, E. M. Shevach, and W. Strober, eds.) pp. 3.1.3–3.1.5. Greene Publishing and Wiley-Interscience, New York.

Lee et al. (1982). *Nature* 294:228.

Mallett, S. et al. (1990). *EMBO* 9(4):1063–1068.

May, R. D., and Fulton, R. J. (1992). *In Vitro Methods of Toxicology* (R. R. Watson, editor) pp. 9–20. CRC Press Inc., Boca Raton, Fla.

McCuthan et al. (1968). *J. Natl Cancer Inst.* 41:351.

Mueller et al. (1978). *Cell* 15:579.

Mulligan and Berg (1981). *Proc. Natl. Acad. Sci. USA* 78:2072–2076.

Mulligan et al. (1981). *Proc. Natl. Acad. Sci. USA* 78:1078–2076.

Neumann et al. (1982). *EMBO J* 1:841.

Oksenberg, J. R. et al. (1993). *Nature* 362:68–70.

Oksenberg, J. R. et al. (1990). *Nature* 345:344–345.

Olsnes and Phil, (1982). "Chimeric Toxins", *Pharm. Therap.* 25:355–381.

Riechmann et al. (1988). *Nature* 332:323–327.

Ruther and Muller-Hill (1983). *EMBO J.* 2:1791.

Sambrook et al. (1989). In *Molecular Cloning: A Laboratory Manual,* Cold Spring Harbor, N.Y.

Sarver et al. (1981). *Mol. Cell Biol.* 1:486.

Schafner (1980). *Proc. Natl. Acad. Sci. USA* 77:2163–2167.

Shimatake and Rosenberg (1981). *Nature* 292:128.

Southern and Berg (1982). *J. Mol. Appl. Genet.* 1:327–341.

Spaete et al. (1982). *Cell* 30:295.

Spliter, L. E. et al. (1987). *Cancer Research* 47:17.17–1723.

Stanley and Luzio (1984). *EMBO J.* 3:1429.

Steinman, L. (1993). *Scientific American* September:107–114.

Street, N. E. et al. (1987). *J. of Immunol.* 139:1734–1738.

Studiar and Moffatt (1986). *J. Mol. Biol.*

Sugden et al. (1985). *Mol. Cell Biol.* 5:410.

Summers and Smith (1985). In *Genetically Altered Viruses and the Environment,* Fields et al. (Eds.) 22:319–328, Cold Spring Harbor Laboratory Press, Cold Spring Harbor, N.Y.

Swanborg, R. H. (1983). *J. Immunol.* 130:503–510.

Thorpe et al. (1982). "Monoclonal Antibody-Toxin Conjugates: Aiming the Magic Bullet," *Monoclonal Antibodies in Clinical Medicine,* Academic Press, pp. 168–190.

Vandenbark, A. A. et al. (1985). *J. Immunol.* 135:223–228.

Veres et al. (1987). *Science* 237:415–417.

Vitetta, E. S. et al. (1991). *Cancer Research* 51:4052–4058.

Weiner et al. (1989). *Cancer Research* 49:4062–4067.

---

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 848 base pairs
      (B) TYPE: Nucleic acid
      (C) STRANDEDNESS: Double
      (D) TOPOLOGY: Linear (ii) MOLECULE TYPE: cDNA to mRNA (iii) HYPOTHETICAL: No (iv) ANTI-SENSE: No (xi) SEQUENCE DESCRIPTION: SEQ ID NO: 1:

```
CGGC AGAGACGAGG     14
ATG TGC GTG GGG GCT CGG CGG CTG GGC CGC GGG CCG TGT GCG GCT            59
met cys val gly ala arg arg leu gly arg gly pro cys ala ala
1               5                   10                  15

CTG CTC CTC CTG GGC CTG GGG CTG AGC ACC GTG ACG GGG CTC CAC           104
leu leu leu leu gly leu gly leu ser thr val thr gly leu his
20              25                  30

TGT GTC GGG GAC ACC TAC CCC AGC AAC GAC CGG TGC TGC CAC GAG           149
cys val gly asp thr tyr pro ser asn asp arg cys cys his glu
35              40                  45

TGC AGG CCA GGC AAC GGG ATG GTG AGC CGC TGC AGC CGC TCC CAG           194
cys arg pro gly asn gly met val ser arg cys ser arg ser gln
50              55                  60

AAC ACG GTG TGC CGT CCG TGC GGG CCG GGC TTC TAC AAC GAC GTG           239
asn thr val cys arg pro cys gly pro gly phe tyr asn asp val
65              70                  75

GTC AGC TCC AAG CCG TGC AAG CCC TGC ACG TGG TGT AAC CTC AGA           284
val ser ser lys pro cys lys pro cys thr trp cys asn leu arg
80              85                  90

AGT GGG AGT GAA CGG AAG CAG CTA TGC ACG GCC ACA CAG GAC ACA           329
ser gly ser glu arg lys gln leu cys thr ala thr gln asp thr
95              100                 105
```

```
GTC TGT CGC TGC CGG GCG GGC ACC CAG TCC CTG GAC AGC TAC AAG        374
val cys arg cys arg ala gly thr gln ser leu asp ser tyr lys
110                 115                 120

CCT GGA GTT GAC TGT GCC CCC TGC CCT CCA GGG CAC TTC TCC CCA        419
pro gly val asp cys ala pro cys pro pro gly his phe ser pro
125                 130                 135

GGC GAC AAC CAG GCC TGC AAG CCC TGG ACC ACC TGT ACC TTG GTT        464
gly asp asn gln ala cys lys pro trp thr thr cys thr leu val
140                 145                 150

GGG AAG CAC ACC CTG CAG CCG GCC AGT AAT AGC TCG GAC GCA ATC        509
gly lys his thr leu gln pro ala ser asn ser ser asp ala ile
155                 160                 165

TGT GAG GAC AGG GAC CCC CCA GCC ACG CAG CCC CAG GAG ACC CAG        554
cys glu asp arg asp pro pro ala thr gln pro gln glu thr gln
170                 175                 180

GGT CCC CCG GCC AGG CCC ATC ACT GTC CAG CCC ACT GAA GCC TGG        599
gly pro pro ala arg pro ile thr val gln pro thr glu ala trp
185                 190                 195

CCC AGA ACC TCA CAG GGA CCC TCC ACC CGG TCC GTG GAG GTC CCC        644
pro arg thr ser gln gly pro ser thr arg ser val glu val pro
200                 205                 210

GGG GGC CGT GCG GTT GCC GCC ATC CTG GGA CTG GGA CTG GTG CTG        689
gly gly arg ala val ala ala ile leu gly leu gly leu val leu
215                 220                 225

GGG CTG CTG GGA CCC CTG GAC ATC CTG CTG GCC CTG TAC CTG ATC        734
gly leu leu gly pro leu asp ile leu leu ala leu tyr leu ile
230                 235                 240

CGG AGG GAC CAG AGG CTG CCC CCC GAT GCC CAC AAG CCC CCT GGG        779
arg arg asp gln arg leu pro pro asp ala his lys pro pro gly
245                 250                 255

GGA GGT AGC TTC CGG ACC CCC ATC CAA GAG GAG CAG GCC GAC GCC        824
gly gly ser phe arg thr pro ile gln glu glu gln ala asp ala
260                 265                 270

CAC TCC ACC CTG GTC AAG TTC TGA                                    848
his ser thr leu val lys phe
275

(2) INFORMATION FOR SEQ ID NO:2:

(i) SEQUENCE CHARACTERISTICS:
        (A) LENGTH:  24 base pairs
        (B) TYPE:  Nucleic acid
        (C) STRANDEDNESS:  Single
        (D) TOPOLOGY:  Linear (iii) HYPOTHETICAL:  No (iv) ANTI-SENSE:  No (xi) SEQUENCE DESCRIPTION:  SEQ ID NO:  2:

ATGTGCGTGG GGGCTCGGCG GCTG                                         24

(2) INFORMATION FOR SEQ ID NO:3:

(i) SEQUENCE CHARACTERISTICS:
        (A) LENGTH:  24 base pairs
        (B) TYPE:  Nucleic acid
        (C) STRANDEDNESS:  Single
        (D) TOPOLOGY:  Linear (iii) HYPOTHETICAL:  No (iv) ANTI-SENSE:  No
```

-continued (xi) SEQUENCE DESCRIPTION: SEQ ID NO: 3:

TCAGAACTTG ACCAGGGTGG AGTG                                           24

(2) INFORMATION FOR SEQ ID NO:4:

(i) SEQUENCE CHARACTERISTICS:
        (A) LENGTH: 277
        (B) TYPE: Amino acid
        (C) STRANDEDNESS: Single
        (D) TOPOLOGY: Linear (xi) SEQUENCE DESCRIPTION: SEQ ID NO: 4:

```
met cys val gly ala arg arg leu gly arg gly pro cys ala ala
1               5                   10                  15 leu leu leu leu gly leu gly leu ser thr val thr gly leu his
20                  25                  30 cys val gly asp thr tyr pro ser asn asp arg cys cys his glu
35                  40                  45 cys arg pro gly asn gly met val ser arg cys ser arg ser gln
50                  55                  60 asn thr val cys arg pro cys gly pro gly phe tyr asn asp val
65                  70                  75 val ser ser lys pro cys lys pro cys thr trp cys asn leu arg
80                  85                  90 ser gly ser glu arg lys gln leu cys thr ala thr gln asp thr
95                  100                 105 val cys arg cys arg ala gly thr gln ser leu asp ser tyr lys
110                 115                 120 pro gly val asp cys ala pro cys pro pro gly his phe ser pro
125                 130                 135 gly asp asn gln ala cys lys pro trp thr thr cys thr leu val
140                 145                 150 gly lys his thr leu gln pro ala ser asn ser ser asp ala ile
155                 160                 165 cys glu asp arg asp pro pro ala thr gln pro gln glu thr gln
170                 175                 180 gly pro pro ala arg pro ile thr val gln pro thr glu ala trp
185                 190                 195 pro arg thr ser gln gly pro ser thr arg ser val glu val pro
200                 205                 210 gly gly arg ala val ala ala ile leu gly leu gly leu val leu
215                 220                 225 gly leu leu gly pro leu asp ile leu leu ala leu tyr leu ile
230                 235                 240 arg arg asp gln arg leu pro pro asp ala his lys pro pro gly
245                 250                 255 gly gly ser phe arg thr pro ile gln glu gln ala asp ala
260                 265                 270 his ser thr leu val lys phe
275
```

We claim:

1. A method of detecting a presence of activated antigen-specific CD4+ T-cells within an inflammatory site in a subject, comprising:

obtaining a body tissue or fluid sample from the inflammatory site; and detecting the presence of OX-40 antigen on the surface of CD4+ T-cells in said tissue or fluid sample, wherein the detecting comprises contacting the tissue or fluid sample with an antibody or a fragment thereof that specifically binds to the human or rat OX40 antigen to detect activated antigen-specific CD4+ T-cells.

2. The method of claim 1, wherein the antibody binds to the human OX-40 antigen.

3. The method of claim 2, wherein the antibody is a polyclonal antibody or a monoclonal antibody or a fragment thereof.

4. The method of claim 3 wherein the antibody or antibody fragment is conjugated with a label molecule to facilitate detection of the antibody or antibody fragment when bound to an OX-40 antigen.

5. The method of claim 4 wherein the label molecule is a fluorescent label.

6. A method of detecting a condition mediated by activated antigen specific CD4+ T-cells in a subject, the method comprising:

obtaining a body tissue or fluid sample from an inflammatory site of a target organ of the condition mediated by activated antigen-specific CD4+ T-cells from the subject; and detecting the presence of OX-40 antigen on the surface of activated antigen specific CD4+ T-cells in said tissue or fluid, wherein the detecting comprises contacting the tissue or fluid sample with an antibody or fragment thereof that specifically binds to the human or rat OX-40 antigen, thereby detecting the condition mediated by activated antigen-specific CD4+ T-cells in the subject.

7. The method of claim 6, wherein the antibody binds to the human OX-40 antigen.

8. The method of claim 7, wherein the antibody is a polylonal antibody or a monoclonal antibody or a fragment thereof.

9. The method of claim 8 wherein the antibody or antibody fragment is conjugated with a label molecule to facilitate detection of the antibody or antibody fragment when bound to an OX-40 antigen.

10. The method of claim 9 wherein the label molecule is a fluorescent label.

11. The method of claim 7, wherein the condition to be detected is selected from the group consisting of multiple sclerosis, sarcoidosis, rheumatoid arthritis, autoimmune uveitis, inflammatory bowel disease and graft-versus-host disease.

12. The method of claim 7, wherein the condition to be detected is multiple sclerosis and the fluid sample is cerebrospinal fluid.

13. The method of claim 7, wherein the condition to be detected is rheumatoid arthritis and the tissue sample is synovial fluid.

14. The method of claim 7, wherein the condition to be detected is graft-versus host disease or transplant rejection and the tissue sample is transplanted tissue.

15. The method of claim 7, wherein the condition to be detected is inflammatory bowel disease and the tissue sample is bowel tissue.

16. The method of claim 2, wherein said obtaining step occurs prior to the onset of clinical symptoms of the condition mediated by activated antigen-specific CD4+ T-cells.

17. A method of detecting the presence of activated antigen-specific CD4+ T-cells in a subject comprising:

obtaining a biological sample from the subject from an inflammatory site of an autoimmune lesion in a target organ of a CD4+ T-cell mediated autoimmune disease; and detecting the presence of OX-40 antigen on the surface of CD4+ T-cells isolated from the biological sample using an antibody specific for the human or rat OX-40 antigen.

18. The method of claim 17, wherein the antibody is specific for the human OX-40 antigen.

19. The method of claim 18, wherein the antibody is a monoclonal antibody.

20. A method of detecting a condition mediated by activated antigen-specific CD4+ T-cells in a subject, the method comprising:

obtaining a biological sample from the subject from an inflammatory site of an autoimmune lesion in a target organ of a CD4+ T-cell mediated autoimmune disease; and detecting the presence of increased expression of an OX-40 antigen on the surface of activated antigen-specific CD4+ T-cells isolated from the biological sample using an antibody specific for the human or rat OX-40 antigen, thereby detecting the presence of the condition.

21. The method of claim 20, wherein the antibody is specific for the human OX-40 antigen.

22. The method of claim 21, wherein the antibody is a monoclonal antibody.

23. The method of claim 7, wherein the subject has an autoimmune disorder mediated by activated antigen-specific CD4+ T-cells.

24. The method of claim 2, wherein the subject has an autoimmune disorder mediated by activated antigen-specific activated CD4+ T-cells.

* * * * *

UNITED STATES PATENT AND TRADEMARK OFFICE
CERTIFICATE OF CORRECTION

PATENT NO. : 6,566,082 B1
DATED : May 20, 2003
INVENTOR(S) : Weinberg et al.

It is certified that error appears in the above-identified patent and that said Letters Patent is hereby corrected as shown below:

Title page,
Item [56], References Cited, OTHER PUBLICATIONS, "W. Godfrey et al." reference, "Identification of a human OX-40 ligand, a a costimulator…" should read
-- 'Identification of a human OX-40 ligand, a costimulator … --

Column 1,
Line 67, "endephalomyelitis" should read -- encephalomyelitis --.

Column 2,
Line 17, "autoimmune." should read -- autoimmune --.

Column 6,
Line 13, "T-celis" should read -- T-cells --.

Column 1,
Line 40, "quadripiegic" should read -- quadriplegic --.

Column 12,
Line 62, "waspositive" should read -- was positive --.

Column 15,
Lines 11 and 66, "4.0" should read -- 40 --.
Line 11, "Abalone" should read -- A alone --.
Line 51, ")." should read -- ) --.
Line 65, "between. the" should read -- between the --.

UNITED STATES PATENT AND TRADEMARK OFFICE
CERTIFICATE OF CORRECTION

PATENT NO. : 6,566,082 B1
DATED : May 20, 2003
INVENTOR(S) : Weinberg et al.

It is certified that error appears in the above-identified patent and that said Letters Patent is hereby corrected as shown below:

Column 16,
Line 31, "dembnstrate" should read -- demonstrate --.

Signed and Sealed this

Twenty-fifth Day of May, 2004

JON W. DUDAS
*Acting Director of the United States Patent and Trademark Office*

UNITED STATES PATENT AND TRADEMARK OFFICE
CERTIFICATE OF CORRECTION

PATENT NO.    : 6,566,082 B1
DATED         : May 20, 2003
INVENTOR(S)   : Weinberg et al.

It is certified that error appears in the above-identified patent and that said Letters Patent is hereby corrected as shown below:

Column 16,
Table Ia, should read as follows:

| | In Vivo Labelling of OX-40 Positive T Cells | | | |
|---|---|---|---|---|
| Treatment[a] / Cell Isolation | $OX\text{-}40^+$ | α-mouse $Ig^+$ | $Donor^+$/$Donar^+$ α-mouse $Ig^+$ | mouse $Ig^+$ |
| Control | | | | |
| Spinal Cord | 17.9%[b] | 0.2% | 54.4% | 0.3% |
| Spleen | 0.5% | 0.3% | 2.4% | 0.2% |
| OX-40 | | | | |
| Spinal Cord | 17.7% | 17.5%[c] | 53.2% | 13.5% |
| Spleen | 0.3% | 0.4% | 4.6% | 0.3% |
| OX-40-Ricin A[d] | | | | |
| Spinal Cord | 19.0% | 18.1% | 50.3% | 18.0% |
| Spleen | 0.7% | 0.5% | 2.3% | 0.4% |

Column 18,
Line 28, "sequenceof" should read -- sequence of --.

Column 19,
Table 3, "PBLS" should read -- PBLs --.
Line 30, "Immunbcytochemistry" should read -- Immunocytochemistry --.
Line 31, "and, Biology" should read -- and Biology --.
Line 42, "OXT-40" should read -- OX-40 --.

Column 20,
Line 52, "Luzid" should read -- Luzio --.

UNITED STATES PATENT AND TRADEMARK OFFICE
CERTIFICATE OF CORRECTION

PATENT NO. : 6,566,082 B1
DATED : May 20, 2003
INVENTOR(S) : Weinberg et al.

It is certified that error appears in the above-identified patent and that said Letters Patent is hereby corrected as shown below:

Column 24,
Line 56, "cytotdxic" should read -- cytotoxic --.

Column 27,
Line 23, "OX-40antigen" should read -- OX-40 antigen --.

Signed and Sealed this

Thirtieth Day of May, 2006

JON W. DUDAS
*Director of the United States Patent and Trademark Office*